United States Patent
Datta et al.

(10) Patent No.: US 9,317,743 B2
(45) Date of Patent: Apr. 19, 2016

(54) SYSTEM AND METHOD FOR AUTOMATICALLY DISCOVERING, CHARACTERIZING, CLASSIFYING AND SEMI-AUTOMATICALLY LABELING ANIMAL BEHAVIOR AND QUANTITATIVE PHENOTYPING OF BEHAVIORS IN ANIMALS

(71) Applicant: PRESIDENT AND FELLOWS OF HARVARD COLLEGE, Cambridge, MA (US)

(72) Inventors: Sandeep Robert Datta, Newton, MA (US); Alexander B. Wiltschko, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/537,246

(22) Filed: Nov. 10, 2014

(65) Prior Publication Data
US 2015/0146939 A1    May 28, 2015

Related U.S. Application Data

(63) Continuation of application No. PCT/US2013/040516, filed on May 10, 2013.

(60) Provisional application No. 61/645,172, filed on May 10, 2012, provisional application No. 61/791,836, filed on Mar. 15, 2013.

(51) Int. Cl.
*G06K 9/00* (2006.01)
*G06T 7/00* (2006.01)
(Continued)

(52) U.S. Cl.
CPC .......... *G06K 9/00362* (2013.01); *A01K 67/00* (2013.01); *G06K 9/00335* (2013.01);
(Continued)

(58) Field of Classification Search
None
See application file for complete search history.

(56) References Cited

U.S. PATENT DOCUMENTS

| 2003/0028327 A1 | 2/2003 | Brunner et al. |
| 2004/0141636 A1 | 7/2004 | Liang et al. |

(Continued)

FOREIGN PATENT DOCUMENTS

| JP | 11-296651 A | 10/1999 |
| JP | 2005-196398 A | 7/2005 |

OTHER PUBLICATIONS

Millot, Sandie, Marie-Laure Bégout, and Béatrice Chatain. "Exploration behaviour and flight response toward a stimulus in three sea bass strains (Dicentrarchus labrax L.)." Applied Animal Behaviour Science 119.1 (2009): 108-114.*

(Continued)

*Primary Examiner* — Stephen R Koziol
*Assistant Examiner* — Raphael Schwartz
(74) *Attorney, Agent, or Firm* — Nixon Peabody LLP; David S. Resnick; Erik Birkeneder

(57) ABSTRACT

A method for studying the behavior of an animal in an experimental area including stimulating the animal using a stimulus device; collecting data from the animal using a data collection device; analyzing the collected data; and developing a quantitative behavioral primitive from the analyzed data. A system for studying the behavior of an animal in an experimental area including a stimulus device for stimulating the animal; a data collection device for collecting data from the animal; a device for analyzing the collected data; and a device for developing a quantitative behavioral primitive from the analyzed data. A computer implemented method, a computer system and a nontransitory computer readable storage medium related to the same. Also, a method and apparatus for automatically discovering, characterizing and classifying the behavior of an animal in an experimental area. Further, use of a depth camera and/or a touch sensitive device related to the same.

15 Claims, 17 Drawing Sheets

BASELINE IMAGE

ACQUIRED IMAGE

(51) Int. Cl.
*A01K 67/00* (2006.01)
*A61B 5/11* (2006.01)
*G06F 19/18* (2011.01)

(52) U.S. Cl.
CPC ......... *G06T7/0016* (2013.01); *A01K 2227/105* (2013.01); *A01K 2267/0356* (2013.01); *A61B 5/112* (2013.01); *A61B 5/1116* (2013.01); *A61B 2503/40* (2013.01); *G06F 19/18* (2013.01); *G06T 2207/10028* (2013.01)

(56) References Cited

U.S. PATENT DOCUMENTS

2008/0152192 A1 6/2008 Zhu et al.
2009/0220425 A1 9/2009 Moxon et al.

OTHER PUBLICATIONS

Ou-Yang, Tai-Hsien, et al. "An infrared range camera-based approach for three-dimensional locomotion tracking and pose reconstruction in a rodent." Journal of neuroscience methods 201.1 (2011): 116-123.*
Xue, Xinwei, and Thomas Henderson. "Video-based animal behavior analysis from multiple cameras." Multisensor Fusion and Integration for Intelligent Systems, 2006 IEEE International Conference on. IEEE, 2006.*
Abrahams et al., "Connecting genes to brain in the autism spectrum disorders", Arch Neurol, 67(4):395-399, (2010).
Benjamini et al., "Ten ways to improve the quality of descriptions of whole-animal movement", Neuroscience and Biobehavioral Reviews, 34:1351-1365, (2010).
Benjamini et al., "Quantifying the buildup in extent and complexity free exploration in mice", PNAS, 108 (3):15580-15587 (2011).
Bill et al., "Genetic advances in autism: heterogeneity and convergence on shared pathways", Current Opinion in Genetics and development, 19:271-278 (2009).
Brennan et al., "Pheromonal communication in vertebrates", Nature, 444:308-315 (2006).
Broad et al., "More to pheromes than meets the nose", Nature Neuroscience, 11(2):28-29 (2008).
Cohen et al., "Communication between the synapse and the nucleus in neuronal development, plasticity, and disease", Annual Rev Cell Dev Biol, 24:183-209 (2008).
Crawley et al., "Mouse behavioral assays relevant to the symptoms of autism", Brian Pathology 17:448-459 (2007).
Crawley, J., "Behavioral phenotyping strategies for mutant mice", Neuron 57:809-818 (2008).
Fairless et al., "Deconstructing sociability, an autism-relevant phenotype, in mouse models", The anatomical record 294:1713-1725 (2011).
Fendt et al., "TMT-induced autonomic and behavioral changes and the neural basis of its processing", Neuroscience and Biobehavioral Reviews, 29:1145-1156 (2005).
Ferrero et al., "The secret codes of mammalian scents", Wiley, 2:23-33 (2010).
Geschwind, D., "Autism: Many genes common pathways?", Cell, 135:391-395 (2008).
Geschwind, D., "Advances in Autism", Annul Rev med., 60:367-380 (2009).
Greer et al., "The Angelman syndrome protein Ube3A regulates synapse development by ubiquitinating arc", Cell, 140:704-716 (2010).
Horev et al., "Dosage-dependent phenotypes in models of 16p11.2 lesions found in autism", 108(41):17076-17081 (2011).
Jhuang et al., "Automated home-cage behavioural phenotyping of mice," Nature Communications 1:68 doi:10.1038/ncomms1064 (2010).
Kimchi et al., "A functional circuit underlying male sexual behavior in the female mouse brain", Nature, 448:1009-1014 (2007).
Kobayakawa et al., "Innate versus learned odour processing in the mouse olfactory bulb", Nature 450:503-510 (2007).
Mandiyan et al., "Deficits in sexual and aggressive behaviors in Cnga mutant mice", Nature Nueroscience, 8(12):1660-1662 (2005).
Moy et al., "Advances in behavioral genetics:mouse models of autism", Molecular Psychiatry, 13:4-26 (2008).
Moy et al., "Social approach in genetically engineered mouse lines relevant to autism", Genes, Brain and Behavior 8:129-142 (2009).
Nestler et al., "Animal models of neuropsychiatric disorders", Nature Neuroscience, 13(1):1161-1169 (2010).
Ou-Yang et al., "An infrared range camera-based approach for three-dimensional locomotion tracking and pose reconstruction in a rodent", Journal of Neuroscience Methods 201:116-123 (2011).
Penagarikano et al., "Absence of CNTNAP2 leads to epilepsy neuronal migration adnormalities and core autism-related deficits", Cell, 147:235-246 (2011).
Peca et al., "Shank3 mutant mice displays autistic-like behaviours and striatal dysfunction", Nature, 472:437-447 (2011).
Radyushkin e al., "Neuroligin-3-deficient mice: model of a monogenic heritable form of autism with an olfactory deficit," Genes, Brain, and Behavior, 8:416-425 (2009).
Restrepo et al., "Emerging views on the distinct but related roles of the main and accessory olfactory systems in responsiveness to chemosensory signals in mice", Hormones and Behavior 46:247-256 (2004).
Ryan et al., "Olfactory cues are sufficient to elicit social approach behaviors but not social transmission of food preference in C57BL/6J mice," Behavioral Brain Research 193:235-242 (2008).
Sudhof et al., "Neuroligins and neurexins link synaptic function to cognitive disease," Nature, 455:903-911 (2008).
Silverman et al., "Behavioural phenotyping assaus for mouse models of autism", Nature Reviews 11:490-502 (2010).
Spink et al., "The EthoVision video tracking system—a tool for behavioral phenotyping of transgenic mice", Physiology & Behavior 73:731-744 (2001).
Steele et al., "The power of automated high-resolution behavior analysis revealed by its applciation to mouse models of huntington's and prion diseases," PNAS, 104(6):1983-1988 (2007).
Stella et al., "Uexkullian umwelt as science and as ideology the light and the dark side of a concept", Theory Biosci. 129:39-51 (2010).
Stowers et al. "Olfactory mechanisms of stereotyped behavior: on the scent of specialized circuits", Current Opinion in Neurobiology, 20:274-280 (2010).
Su et al., "Olfactory perception: receptors, cells, and circuits", Cell, 139:45-59 (2009).
Verbeek et al., "Rodent behavior annotation from video", Technical Report, ISA-UVA-05-2, pp. 18 (2005).
Walsh et al., "Autism and brain development", Cell, 135:396-400 (2008).
Wang et al., "Pheromone detection in male mice depends on signaling through the type 3 adenylyl cyclase in the main olfactory epithelium", The Journal of Neuroscience, 26(28):7375-7379 (2006).
Wang et al., "Are you pheromones detected through the main olfactory epithelium", Mol Neurobiol 35:317-323 (2007).
Witt et al., "Olfactory behavioral testing in the adult mouse", Journal of Visualized Experiments, 1-5 (2009).
Yang et al., "Simple behavioral assessment of mouse olfaction", Current protocols in Neuroscience 8.24.1 Supplement 48 (2009).
Yildirim et al., "TRPC2: Molecular biology and functional importance", HEP 179:53-75 (2007).
Mayya et al., "Visual tracking of small animals based on real-time level set method with fast infra-red thermographic imaging", Rose 2011, IEEE International Symposium on Robotic and Sensors Environments Proceedings, Sep. 17-18, 2011.

* cited by examiner

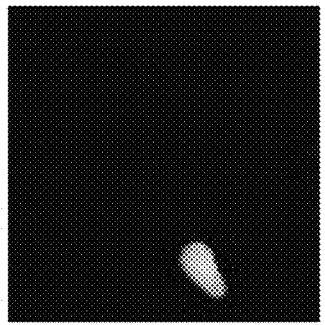
FIG. 1A BASELINE IMAGE
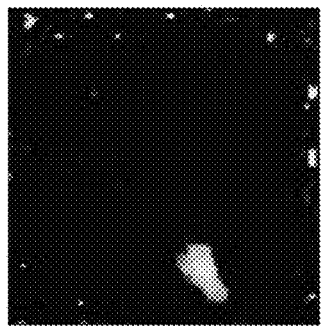
FIG. 1B ACQUIRED IMAGE
FIG. 1C BASELINE SUBTRACTED IMAGE
FIG. 1D AFTER MEDIAN FILTERING
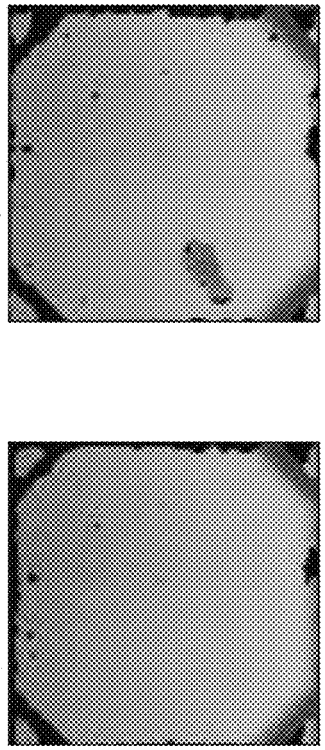
FIG. 1E CONTOUR IDENTIFICATION
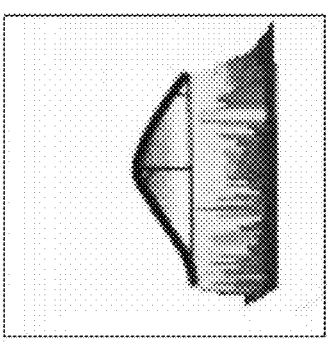
FIG. 1F CONNECTION OF ANIMAL CONTOUR
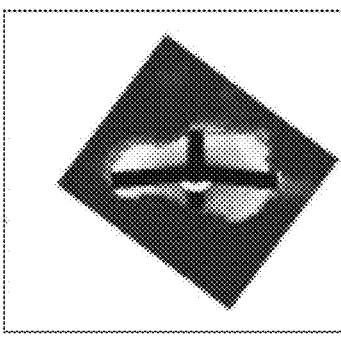
FIG. 1G EXTRACTION OF TOP DOWN FEATURES
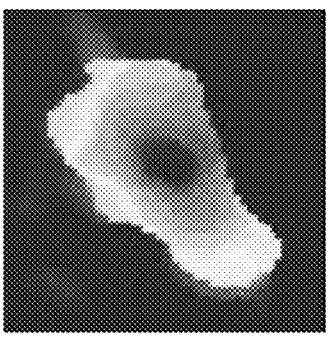
FIG. 1H EXTRACTION OF SIDE VIEW FEATURES

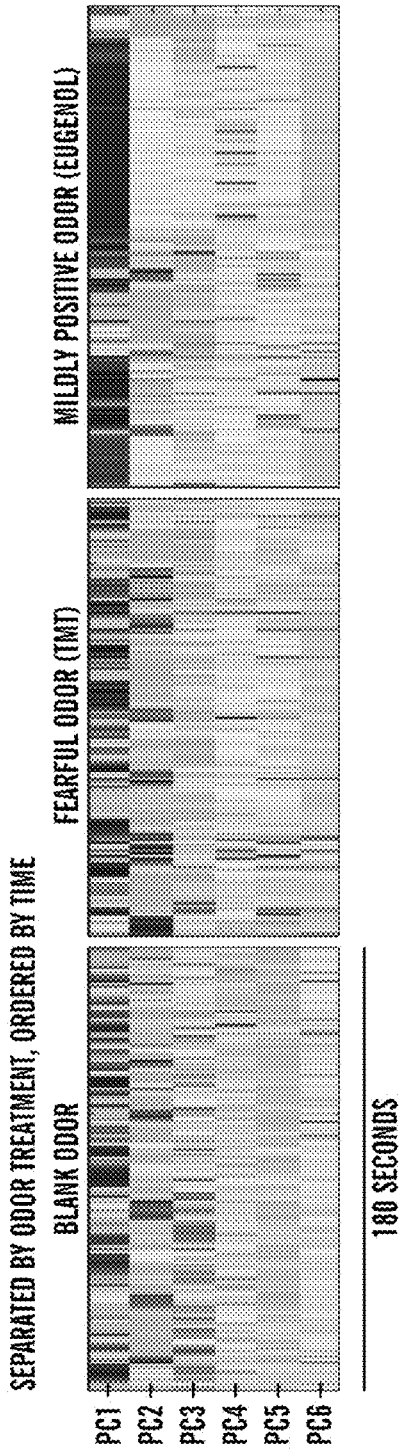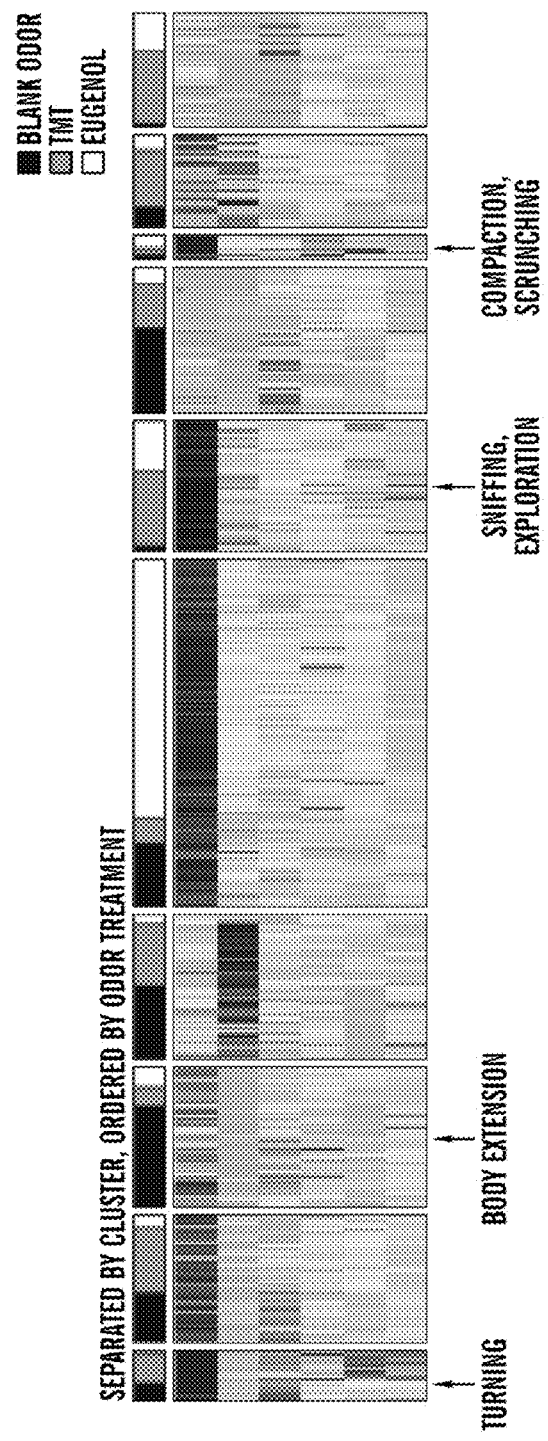
FIG. 2A
FIG. 2B

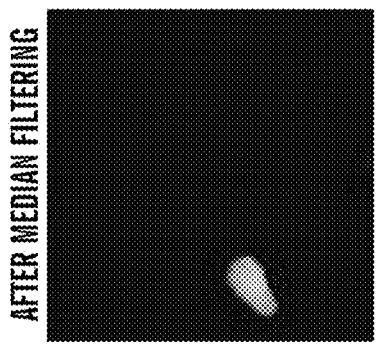
FIG. 5D
AFTER MEDIAN FILTERING
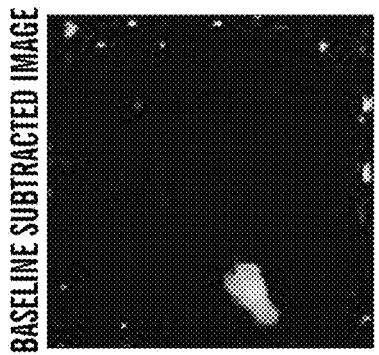
FIG. 5C
BASELINE SUBTRACTED IMAGE
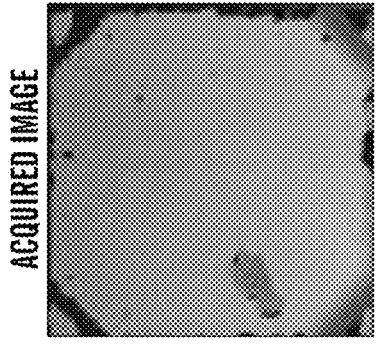
FIG. 5B
ACQUIRED IMAGE
FIG. 5A
BASELINE IMAGE
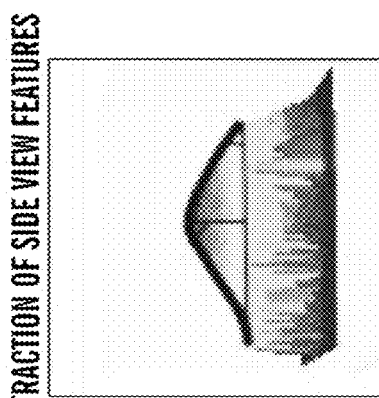
FIG. 5H
EXTRACTION OF SIDE VIEW FEATURES
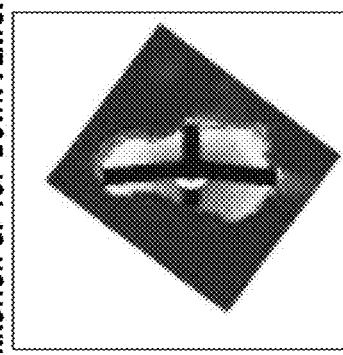
FIG. 5G
EXTRACTION OF TOP DOWN FEATURES
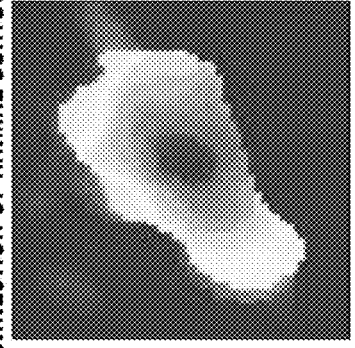
FIG. 5F
CONNECTION OF ANIMAL CONTOUR
FIG. 5E
CONTOUR IDENTIFICATION

SYSTEM AND METHOD FOR AUTOMATICALLY DISCOVERING, CHARACTERIZING, CLASSIFYING AND SEMI-AUTOMATICALLY LABELING ANIMAL BEHAVIOR AND QUANTITATIVE PHENOTYPING OF BEHAVIORS IN ANIMALS

CROSS-REFERENCES TO RELATED APPLICATIONS

This application is a continuation of International Patent Application No. PCT/US13/40516, filed May 10, 2013, entitled "A SYSTEM AND METHOD FOR AUTOMATICALLY DISCOVERING, CHARACTERIZING, CLASSIFYING AND SEMI-AUTOMATICALLY LABELING ANIMAL BEHAVIOR AND QUANTITATIVE PHENOTYPING OF BEHAVIORS IN ANIMALS," the entire disclosure of which is hereby incorporated herein by reference, which claims the benefit under 35 U.S.C. §119(e) of U.S. Provisional Patent Application No. 61/645,172, filed on May 10, 2012, entitled "A SYSTEM AND METHOD FOR AUTOMATICALLY DISCOVERING, CHARACTERIZING, CLASSIFYING AND SEMI-AUTOMATICALLY LABELING ANIMAL BEHAVIOR," the entire disclosure of which is hereby incorporated herein by reference; and U.S. Provisional Patent Application No. 61/791,836, filed on Mar. 15, 2013, entitled "A SYSTEM AND METHOD FOR AUTOMATICALLY DISCOVERING, CHARACTERIZING, CLASSIFYING AND SEMI-AUTOMATICALLY LABELING ANIMAL BEHAVIOR WITH A TOUCH SCREEN," the entire disclosure of which is hereby incorporated herein by reference.

GOVERNMENT SUPPORT

This invention was made with government support under (1) National Institutes of Health (NIH) New Innovator Award No. DP2OD007109 awarded by the NIH Office of the Director; and (2) NIH Research Project Grant Program No. RO1DC011558 awarded by the NIH National Institute on Deafness and Other Communication Disorders (NIDCD). The government has certain rights in the invention.

TECHNICAL FIELD

The quantification of animal behavior is an essential first step in a range of biological studies, from drug discovery to understanding neurodegenerative disorders. It is usually performed by hand; a trained observer watches an animal behave, either live or on videotape, and records the timing of all interesting behaviors. Behavioral data for a single experiment can include hundreds of mice, spanning hundreds of hours of video, necessitating a team of observers, which inevitably decreases the reliability and reproducibility of results. In addition, what constitutes an "interesting behavior" is essentially left to the human observer: while it is trivial for a human observer to assign an anthropomorphic designation to a particular behavior or series of behaviors (i.e., "rearing," "sniffing," "investigating," "walking," "freezing," "eating," and the like), there are almost certainly behavioral states generated by the mouse that are relevant to the mouse that defy simple human categorization. In more advanced applications, video can be semi-automatically analyzed by a computer program. However, all existing computerized systems work by matching parameters describing the observed behavior against hand-annotated and curated parametric databases that include behaviors of interest. So unfortunately, in both the manual and existing semi-automated cases, a great deal of subjective evaluation of the animal's behavioral state is built into the system—a human observer must decide ahead of time what constitutes a particular behavior. This both biases assessment of that behavior and limits the assessment to those particular behaviors the researcher can obviously identify by eye. In addition the video acquisition systems deployed in these semi-supervised forms of behavioral analysis (nearly always acquiring data in two-dimensional) are usually very specific to the behavioral arena being used, thereby both limiting throughput and increasing wasted experimental effort through alignment errors.

Therefore, there is a need for a more objective system for evaluating animal behavior.

Also, Autism Spectrum Disorders (ASDs) are heterogeneous neurodevelopmental syndromes characterized by repetitive behaviors and deficits in the core domains of language development and social interactions [1][2][3]. Association, linkage, expression and copy number variation studies in humans have implicated a number of gene mutations in the development of ASDs, which has led to the engineering of mice harboring orthologous gene defects [2][4][5][6][7]. Because the diagnostic criteria for ASDs are behavioral, validation and use of these mouse models requires detailed behavioral phenotyping that quantitates both solitary and social behaviors [8][9]. However, current behavioral phenotyping methods have significant limitations, both in the manner in which the data are acquired (often through the use of arena-specific 2D cameras) and in the manner in which the datastreams are analyzed (often through human-mediated classification or reference to human-curated databases of annotated behavior). Paradoxically, current methods also offer only the crudest assessment of olfactory function, which is the main sensory modality used by mice to interact with their environment, and the primary means through which social communication is effected in rodents [10][11][12][13][14][15].

SUMMARY OF THE INVENTION

In accordance with the principles of the invention, a monitoring method and system uses affordable, widely available hardware and custom software that can classify animal behavior with no required human intervention. All classification of animal behavioral state is built from quantitative measurement of animal posture in three-dimensions using a depth camera. In one embodiment, a 3D depth camera is used to obtain a stream of video images having both area and depth information of the experimental area with the animal in it. The background image (the empty experimental area) is then removed from each of the plurality of images to generate processed images having light and dark areas. The contours of the light areas in the plurality of processed images are found and parameters from both area and depth image information within the contours is extracted to form a plurality of multi-dimensional data points, each data point representing the posture of the animal at a specific time. The posture data points are then clustered so that point clusters represent animal behaviors.

In another embodiment, the covariance between data points is reduced prior to clustering.

In still another embodiment, the covariance between data points is reduced prior to clustering by reducing the dimensionality of each data point prior to clustering.

In yet another embodiment, clustering is performed by applying a plurality of clustering algorithms to the data and using a metric to select the best results.

In still another embodiment, the plurality of posture data points are scanned with a search algorithm in a sliding window with a fixed time duration, the data points are saved in regular intervals, and clustering is performed on saved periods of posture data points to capture dynamic behavior.

In another embodiment, the plurality of posture data points are scanned with a search algorithm in a plurality of sliding windows, each with a different time duration and for each window, data points are saved in regular intervals. Clustering is then performed on saved periods of posture data points to produce outputs. A metric is used to evaluate the outputs and one time duration is selected based on the evaluations.

To address the significant limitations of existing approaches, the present inventors have developed a system that uses custom software coupled with affordable, widely available video hardware to rapidly and accurately classify animal behavior with no required human intervention. This system circumvents the problem of requiring specific video cameras perfectly aligned to behavioral arenas by taking advantage of range cameras (such as the inexpensive and portable Microsoft Kinect), which use structured illumination and stereovision to generate three-dimensional video streams of rodents; these cameras are incredibly flexible and can be easily adapted to most behavioral arenas, including those used to assess home cage behavior, open field behavior, social behaviors and choice behaviors. The software the present inventors have developed can effectively segment individual mice from the arena background, determine the orientation of the rodent (defining head and tail), and then quantitatively describe its three-dimensional contour, location, velocity, orientation and more than 20 additional morphological descriptors, all in realtime at, for example, 30 frames per second. Using this morphometric information the present inventors have developed algorithms that identify mathematical patterns in the data that are stable over short timescales, each of which represents a behavioral state of the animals (FIG. 8). The present inventors refer to each of these mathematical clusters as QBPs—Quantitative Behavioral Primitives—and can demonstrate that complex behaviors can be represented as individual QBPs or sequences of QBPs; one can use these QBPs to automatically and in real-time detect stereotyped postures and behaviors of mice, and by referring back to the original video one can trivially assign meaningful plain-English labels, like "rearing" or "freezing".

The use of depth cameras has been employed superficially by other research groups, most recently by a Taiwanese group [24]. However, as of the filing of the present patent application, no one has used depth cameras to unambiguously discriminate animal behavioral states that would be impossible to discern with standard 2D cameras. Separately, recent work has expanded the robustness of semi-automated rodent phenotyping with regular cameras [28], and methods for video-rate tracking of animal position have existed for decades. However, there is no successful method the present inventors are aware of besides the present method that combines high temporal precision and rich phenotypic classification, and is further capable of doing so without human supervision or intervention.

In order to ensure that algorithms according to the present invention work seamlessly with other commercially available depth cameras, the present inventors acquired time-of-flight range cameras from major range camera manufacturers such as PMDTec, Fotonic, Microsoft and PrimeSense. The present inventors have established a reference camera setup using the current-generation Microsoft Kinect. Also, the algorithms of the present invention can mathematically accommodate datastreams from other cameras. Comparable setups are established to ensure effective compatibility between the software of the present invention and other types of range video inputs. Small alterations to the algorithms of the present invention can be necessary to ensure consistent performance and accuracy. The present inventors tested each camera against a reference experimental setup, where a small object is moved through an open-field on a stereotyped path. All cameras produce the same 3D contour of the moving object, as well as similar morphometric parameters.

Client-side software was developed, which exposes the algorithms of the present invention using a graphical user interface. A software engineer with experience in machine vision and GUI programming was hired, as well as a user experience engineer with expertise in scientific software usability. One goal of the present invention is to create a client-side software package with minimal setup and high usability. The present inventors developed a GUI and a data framework that enable setup of the software to take under an hour for a naïve user, and data collection within a day. Previous experiments are searchable, and users can export their data into a variety of formats, readable by commonly-used analysis programs, e.g., Matlab or Excel.

Also, regarding ASD, to address the above-referenced issues the present inventors have developed a novel behavioral analysis platform that couples high-resolution (and enclosure-independent) 3D depth cameras with analytic methods that extract comprehensive morphometric data and classify mouse behaviors through mathematical clustering algorithms that are independent of human intervention or bias. Because of the singular importance of the olfactory system to mouse behavior, the present inventors have also built the first apparatus that enables robust quantitation of innate attraction and avoidance of odors delivered in defined concentrations in gas phase. The present inventors use these new methods to perform quantitative behavioral phenotyping of wild-type and ASD model mice (including mice with deletions in Shank3 and Neuroligin3) [16][17]. These experiments include comprehensive analysis of home cage, juvenile play and social interaction behaviors using the unbiased quantitative methods of the present invention; in addition the present inventors use an olfactometer-based odor delivery arena to assess whether innate behavioral responses to defined odorants are altered. The present invention represents an ambitious attempt to bring state-of-the-art machine vision methods to rodent models of disease. Furthermore the collected raw morphometric and classified behavioral data constitute a significant resource for ASD researchers interested in understanding how behavioral states can regulated by ASD candidate genes and by sensory cues relevant to social behaviors.

In one aspect, provided herein is a method for studying the behavior of an animal in an experimental area, comprising: stimulating the animal using a stimulus device; collecting data from the animal using a data collection device; analyzing the collected data; and developing a quantitative behavioral primitive from the analyzed data.

In one embodiment of this aspect, the animal is a mouse.

In another embodiment of this aspect, the mouse is wild or specialized.

In another embodiment of this aspect, the specialized mouse is an ASD mouse.

In another embodiment of this aspect, the ASD mouse is a Shank3 null model or a Neurologin3 null model.

In another embodiment of this aspect, the stimulus device comprises an audio stimulus device, a visual stimulus device or a combination of both.

In another embodiment of this aspect, the stimulus device comprises a means for administering a drug to the animal.

In another embodiment of this aspect, the stimulus device comprises a food delivery system.

In another embodiment of this aspect, the stimulus device comprises an olfactory stimulus device.

In another embodiment of this aspect, the data collection device comprises a depth camera.

In another embodiment of this aspect, the data collection device comprises a tactile data collection device.

In another embodiment of this aspect, the data collection device comprises a pressure sensitive pad.

In another embodiment of this aspect, the collected data from the depth camera is analyzed using a data reduction technique, a clustering approach, a goodness-of-fit metric or a system to extract morphometric parameters.

In another embodiment of this aspect, the collected data from the tactile data collection device is analyzed using a data reduction technique, a clustering approach, a goodness-of-fit metric or a system to extract morphometric parameters.

In another embodiment of this aspect, the developed quantitative behavioral primitive is identified by a human with a natural language descriptor after development of the quantitative behavioral primitive.

In another aspect, provided herein is a system for studying the behavior of an animal in an experimental area, comprising: a stimulus device for stimulating the animal; a data collection device for collecting data from the animal; a device for analyzing the collected data; and a device for developing a quantitative behavioral primitive from the analyzed data.

In one embodiment of this aspect, the animal is a mouse.

In another embodiment of this aspect, the mouse is wild or specialized.

In another embodiment of this aspect, the specialized mouse is an ASD mouse.

In another embodiment of this aspect, the ASD mouse is a Shank3 null model or a Neurologin3 null model.

In another embodiment of this aspect, the stimulus device comprises an audio stimulus device, a visual stimulus device or a combination of both.

In another embodiment of this aspect, the stimulus device comprises a means for administering a drug to the animal.

In another embodiment of this aspect, the stimulus device comprises a food delivery system.

In another embodiment of this aspect, the stimulus device comprises an olfactory stimulus device.

In another embodiment of this aspect, the data collection device comprises a depth camera.

In another embodiment of this aspect, the data collection device comprises a tactile data collection device.

In another embodiment of this aspect, the data collection device comprises a pressure sensitive pad.

In another embodiment of this aspect, the collected data from the depth camera is analyzed using a data reduction technique, a clustering approach, a goodness-of-fit metric or a system to extract morphometric parameters.

In another embodiment of this aspect, the collected data from the tactile data collection device is analyzed using a data reduction technique, a clustering approach, a goodness-of-fit metric or a system to extract morphometric parameters.

In another embodiment of this aspect, the developed quantitative behavioral primitive is identified by a human with a natural language descriptor after development of the quantitative behavioral primitive.

In another aspect, provided herein is a computer implemented method for studying the behavior of an animal in an experimental area, comprising: on a computer device having one or more processors and a memory storing one or more programs for execution by the one or more processors, the one or more programs including instructions for: stimulating the animal using a stimulus device; collecting data from the animal using a data collection device; analyzing the collected data; and developing a quantitative behavioral primitive from the analyzed data.

In another aspect, provided herein is a computer system for studying the behavior of an animal in an experimental area, comprising: one or more processors; and memory to store: one or more programs, the one or more programs comprising: instructions for: stimulating the animal using a stimulus device; collecting data from the animal using a data collection device; analyzing the collected data; and developing a quantitative behavioral primitive from the analyzed data.

In another aspect, provided herein is a nontransitory computer readable storage medium storing one or more programs configured to be executed by one or more processing units at a computer comprising: instructions for: stimulating the animal using a stimulus device; collecting data from the animal using a data collection device; analyzing the collected data; and developing a quantitative behavioral primitive from the analyzed data.

BRIEF DESCRIPTION OF THE DRAWINGS

The accompanying drawings, which are incorporated into this specification, illustrate one or more exemplary embodiments of the inventions disclosed herein and, together with the detailed description, serve to explain the principles and exemplary implementations of these inventions. One of skill in the art will understand that the drawings are illustrative only, and that what is depicted therein may be adapted based on the text of the specification and the spirit and scope of the teachings herein.

In the drawings, like reference numerals refer to like reference in the specification.

FIG. 1A is an exemplary baseline depth image acquired by a 3D depth camera of an experimental area before the start of an experiment.

FIG. 1B is a depth image captured during the experiment in the same experimental area.

FIG. 1C is a difference image produced by subtracting the baseline depth image of FIG. 1A from the depth image shown in FIG. 1B.

FIG. 1D is a filtered difference image generated by performing a median filtering operation on the difference image of FIG. 1C.

FIG. 1E is a processed image created by removing image data values that are less than a predetermined threshold from the filtered difference image of FIG. 1D to create a binary representation of all new additions to the experimental area, which is used to detect the contour of the experimental animal, outlined here in green.

FIG. 1F is a contour of an animal of interest extracted from the processed image with depth data shown as pseudocolor.

FIG. 1G illustrates some simple measurements calculated from an animal top down body view including the animal's perimeter, surface area rotation angle and length.

FIG. 1H illustrates the depth profile of an animal calculated from the depth information in the contour of FIG. 1F.

FIG. 2A shows plots of six principle components (PC1-PC6) versus time generated when a mouse was presented with several different odor treatments.

FIG. 2B shows the data of FIG. 2A clustered in accordance with the principles of the invention irrespective of the odor treatment.

FIGS. 4A and B depict a conventional two-compartment behavioral choice assay. FIG. 4C, left, depicts a new behavioral arena. FIG. 4C, right, depicts a chart generated through use of custom-written Matlab code to track animal trajectories. FIG. 4D, left, depicts the qualitative results of delivering the fox odor TMT in the upper right corner causing avoidance behavior. FIG. 4D, right, depicts the quantitative results of delivering the fox odor TMT in the upper right corner causing avoidance behaviors. In FIG. 4E, re-imaging the apparatus shown in FIG. 4C using a depth camera, and plotting aspect ratio versus height (with time heatmapped) reveals that under control conditions mice stay stretched and low to the ground (FIG. 4E, left) consistent with normal exploratory behaviors, but when confronted with a salient odor like TMT become compressed (from the perspective of the overhead camera) and elevate their noses (FIG. 4E, right), consistent with sniffing events (black arrow).

FIGS. 5A-5H depict the use of depth cameras to acquire and segment 3D video data of mouse behavior. FIG. 5A depicts a baseline image. FIG. 5B depicts an acquired depth image. FIG. 5C depicts a baseline subtracted image. FIG. 5D depicts the subtracted images after median filtering. FIG. 5E depicts contours outlined using a detection algorithm after taking thresholds that distinguish figure from ground. FIG. 5F depicts a 3D image of a mouse extracted using the derived contours. FIG. 5G depicts extraction of top-down features. FIG. 5H depicts extraction of side-view features.

FIG. 9A depicts raw parameter data from FIG. 8 subject to PCA, and six principal components were found to account for most of the variance in posture (each frame is approximately 40 ms, capture rate 24 fps, data is heatmapped). FIG. 9B depicts the behavior of the mouse clustered using K-means clustering (independent of stimulus), and different treatments were found to preferentially elicit different behaviors (white, grey and black bars above).

FIG. 13A depicts raw contour data extracted from a depth camera image of a mouse. FIG. 13B depicts smoothing of the raw mouse contour using B-splines. FIG. 13C depicts plotting curvature measurements. FIG. 13D depicts the taking of an additional derivative, which identifies the less curved tail and the more curved head without supervision.

FIG. 14, Top, depicts the use of the algorithms described in FIGS. 13A-13D to segment, identify and track two separate mice in the same experiment while following their head and tail, which allows measurements of head-head and head-tail interaction. FIG. 14, Bottom, depicts the use of volume rendering of simultaneous tracking of two animals over time; three matched time points are shown as volumes, and average position is represented as color on the ground. Note this representation captures a tail-tail interaction between the two mice.

DETAILED DESCRIPTION

Figure 3:
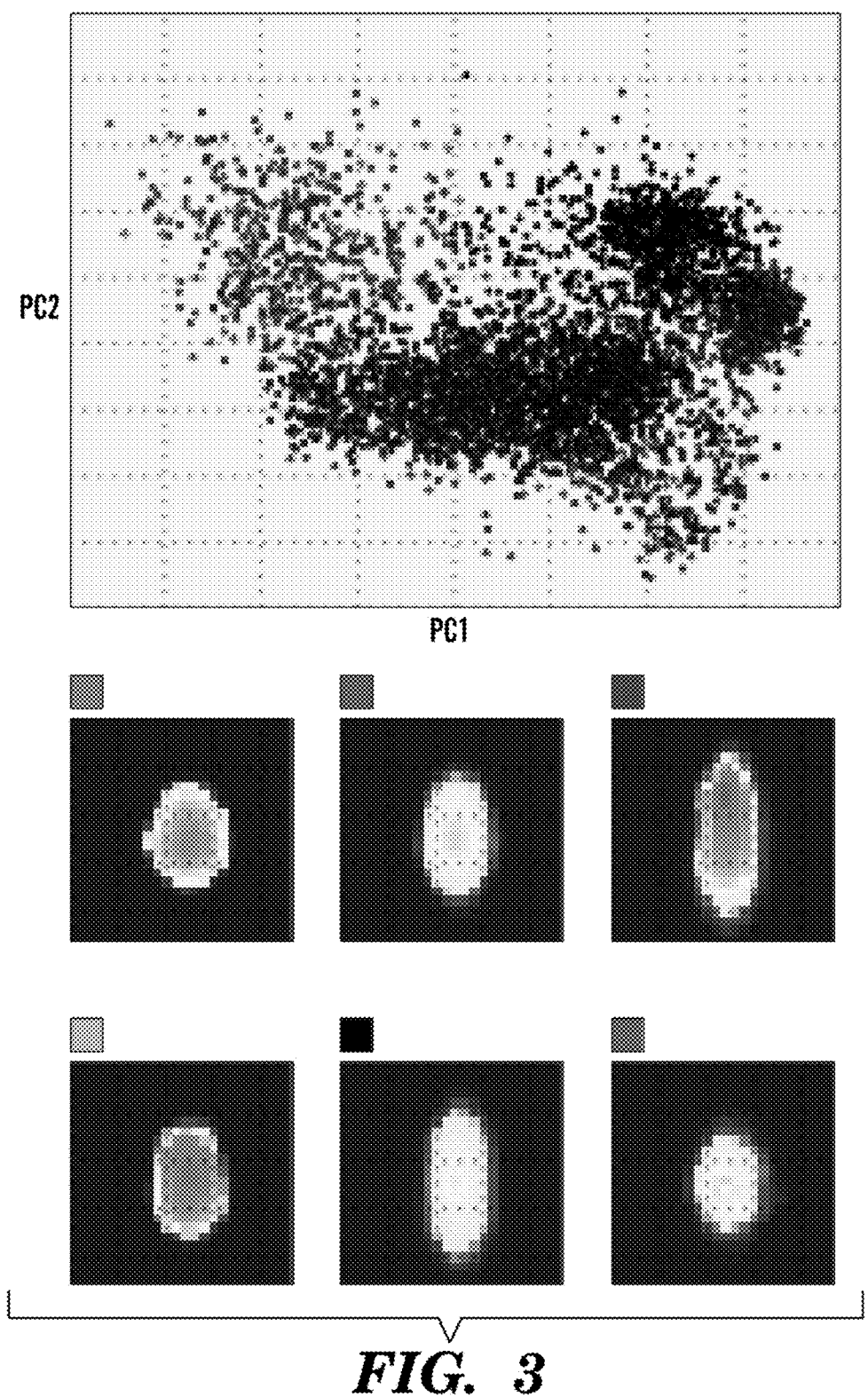
FIG. 3 is a scatterplot of postural variables extracted from a video stream that have been dimensionally reduced to two principle components, PC1 and PC2 showing that stereotyped postures appear as clusters in the principle component space. The clusters are shown below the scatterplot.

It should be understood that this invention is not limited to the particular methodology, protocols, and the like, described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities used herein should be understood as modified in all instances by the term "about."

All publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. Although some portions of the present disclosure refer to mice, the present invention can be applied to any animal, including any mammal, including rats, humans and non-human primates.

In some embodiments, the subject is a mammal. The mammal can be a human, non-human primate, mouse, rat, dog, cat, horse, or cow, but are not limited to these examples. Mammals other than humans can be advantageously used as subjects that represent animal models of disorders.

A subject can be one who has been previously diagnosed with or identified as suffering from or having a disease or disorder caused by any microbes or pathogens described herein. By way of example only, a subject can be diagnosed with sepsis, inflammatory diseases, or infections.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Part One: A System and Method for Automatically Discovering, Characterizing, Classifying and Semi-Automatically Labeling Animal Behavior Including Use of a Depth Camera and/or a Touch Screen A system constructed in accordance with the principles of the invention comprises four key components: (1) a depth camera, such as (but not limited to) a Kinect range camera, manufactured and sold by Microsoft Corporation or a DepthSense infrared time-of-flight camera, manufactured and sold by SoftKinetic, Brussels, Belgium, for generating a 3D video stream data that captures the disposition of an animal within any given behavioral arena, (2) robust animal identification from this 3D video stream, (3) extraction of meaningful parameters from the 3D contour of the animal, including, but not limited to, surface area, volume, height, 3D spine curvature, head direction, velocity, angular velocity and elongation and (4) automated extraction of stereotyped combinations of the above features, which are intuited as postures or behavioral states that are characteristic to the species.

There are two depth camera types—Kinect-style projected depth sensing, and time-of-flight depth detection. The Kinect-style camera can work with animals that have hair. For finer motor analysis, time-of-flight cameras can be used to obtain higher resolution on hairless mice.

Depth cameras are insensitive to laboratory lighting conditions. The room can be dark or light, and the subject animal and the background upon which the subject animal walks can be any color, and the method works with the same fidelity.

For example, in a mouse, a curved spine, small surface area and low height would be a stereotyped feature set that indicates crouching or freezing. In a human, an example posture would be a small convex perimeter, highly curved spine, supine position and low height, which describes a "fetal" position. Note that, while these postures can be described post-hoc with anthropomorphic terms such as "freezing" or "fetal position," for the purposes of analysis this is not required: each defined cluster of mathematical descriptors for the animals' behavior can be used to define a particular behavioral state independent of the ability of an unbiased observer to describe that cluster with a discrete natural language term, either statically, or over time, dynamically.

Taken together, items (1)-(4) constitute a system for automatically discovering, characterizing, classifying and semi-automatically labeling animal behavior for a particular species. In the example case of a mouse, the animal is tracked using a 3D depth camera both before and after some experimental intervention (or two animals are compared that represent two separate experimental conditions). As described below, software enables automatic identification of the animal within this video stream, and a large number of real-time parameters that describe the animal's behavioral state are automatically extracted from the video data. These parameters are subject to a variety of mathematical analyses that enable effective clustering of these parameters; each of these clusters represents a specific behavioral state of the animal. Analysis software can both identify these clusters and characterize their dynamics (i.e., how and with what pattern the animal transitions between each identified behavioral state). Because the identification of these states is mathematical and objective, no prior knowledge about the nature of the observed behavior is required for the software to effectively compare the behaviors elicited in two separate experimental conditions. Thus this invention enables completely unbiased quantitative assessment of behavior.

Although the system is designed to work without human intervention to characterize behavioral states, there are many circumstances in which natural language descriptors of the identified behavioral states would be beneficial. To aid in the natural language assessment of each behavioral cluster (a salutary, although as noted above, not strictly necessary aspect of analysis) the software (potentially operating over a server) acts on a large corpus of recorded 3D video data of a single species of animal, called a "training set" for that species. The software automatically analyzes the behavioral repertoire of the animals in the training set.

Because of the nature of the initial data acquisition with the depth camera, the data contained within this training set has a level of detail that does not exist in other behavioral analysis platforms. Since the mouse is visualized in three-dimensions, the software can tell the difference between behaviors that would be impossible to disambiguate with a single overhead 2D camera. For example, when a mouse is rearing, grooming or freezing, his outline is nearly indistinguishable between all three states. This problem is eliminated with a 3D depth camera, and further all of these behavioral states are automatically "clustered" and separated.

To validate this approach to date dozens of hours of their freely ranging behavior have been recorded, as well as behavior in response to various odors, and a set of stereotyped behavioral clusters have been identified to which plain-language labels have been assigned. As mentioned above, analysis software identifies these clusters by first extracting, for each recorded frame of 3D video of an animal, physical parameters describing the animal's posture: elongation, height, spine curvature, speed, turning speed, and surface area, among many others. Each frame of video can then be viewed as a point, or observation, in a multi-dimensional "posture space". The software then applies a variety of clustering algorithms to all the recorded observations from all animals of a single species to find stereotyped postures. By looking at frames selected from single clusters, it can be seen that clusters can be given plain-language names describing the observed behavior in that cluster. For instance, in one cluster, mice were found standing up on their hind legs, extending their body upwards, which is a behavior called "rearing", and in another cluster they were found crouched and compacted with their spine highly curved, making no movement, which is a behavior called "freezing". These clusters are distinct in postural space, demonstrating that natural language descriptions of animal behavior can be reliably and repeatably extracted over time.

Data generated by the inventive system can be analyzed both statically and dynamically. Statically, a set of behavioral clusters that define the animal's behavior over a period of baseline observation can be generated. An investigation can then be conducted into how the overall behavioral state of the animal changes (these changes are measured as alterations in the density and distribution of the animal's postural clusters) when the animal is offered a particular stimulus (including but not limited to odors, tastes, tactile stimuli, auditory stimuli, visual stimuli, stimuli designed to cause the animal pain or itch), when the animal is offered pharmacological agents designed to mitigate the behavioral effects of those stimuli (including but not limited to agents that alter sensory perception of pain, itch, gustatory, olfactory, auditory and visual cues), or when tests involve animals in which genes are altered that may affect either basal or stimulus-driven behaviors, or behaviors affected by neuroactive pharmacological agents.

Dynamically, changes in the overall behavioral state of the animal can be identified by examining the probabilities for which the animal transitions between postural clusters (under the conditions described above). These two modes of analysis mean that the behavioral analysis approach (depth camera combined with analysis software) is broadly applicable to quantitation of the behavioral consequence of nearly any stimulus or pharmacological or genetic (or optogenetic) manipulation in an unbiased manner.

The inventive method proceeds as follows. First, a model of the experimental area in which the animal will be studied is built using a 3D depth camera and saved as the "baseline depth image". This typically requires recording less than a minute of video of an empty experimental area resulting in an accumulated set of depth images. Then, the median or mean of the corresponding pixel values in the images is calculated over the set of images and used as the corresponding pixel value in the baseline depth image. An exemplary baseline depth image is illustrated in FIG. 1A. The baseline image can be captured and calculated as the median value of a few dozen seconds of video of an empty experimental area.

Images are continuously acquired during the experiment. For every subsequent depth image captured during the experiment in the same experimental area, for example, the depth image shown in FIG. 1B, the baseline depth image is subtracted to produce the difference image shown in FIG. 1C.

The difference image of FIG. 1C on its own can be too noisy for analysis. A median filtering operation can then be performed on the difference image to generate a filtered difference image such as that shown in FIG. 1D. This processing removes noise that is characteristic of depth-sensing range cameras like the Kinect or time-of-flight type 3D depth cameras, such as the DepthSense cameras.

Instead of a median filtering operation to remove background noise, object detection can be used. For example, Haar cascade object detector can be used.

As shown in FIG. 1E, the animal in the experimental area can be identified by taking a threshold, and applying a contour detection algorithm. Specifically, image data values that are less than a predetermined threshold are then removed to create a binary representation of all new additions to the experimental area. Next, the contours of all light regions in this processed image (shown in FIG. 1E) are determined using a conventional border following algorithm. An algorithm suitable for use with the invention is described in detail in an article entitled "Topological Structural Analysis of Digitized Binary Images by Border Following", S. Suzuki and K. Abe, Computer Vision, Graphics and Image Processing, v. 30, pp 32-46 (1983) which article is hereby incorporated by reference in its entirety. Each contour defines a lasso around an animal of interest that has been placed in the experimental area. All further analysis is performed on the depth data contained within these contours (one of which is shown in FIG. 1F where the depth data or depth profile of a mouse is shown in pseudocolor). As shown in FIG. 1F, an image of an animal, such as a mouse, can be extracted.

The method learns in subsequent frames, after an animal has been tracked successfully for several seconds, what to expect the animal to look like, and where it might be in the future using a Kalman filter to track a continuously-updated B-spline smoothing of the animal's contour. More specifically, at each video frame, the mouse's contour is detected, and a small region-of-interest surrounding the mouse is extracted from the background-subtracted image and aligned so the mouse nose is always facing to the right. This rotated, rectangular crop around the mouse serves as the raw data for the dimensionality reduction and clustering algorithms described below.

Movement is analyzed in a similar manner, except instead of extracting the region-of-interest from the background-subtracted frame, it is extracted from an image formed by the difference between the current and previous background-subtracted frames. Regions the mouse is moving towards are designated as positive values, and regions the mouse is leaving are designated as negative values. This processing allows the software to greatly reduce the computational expense of tracking the animal, freeing up resources for more sophisticated live analyses.

Simple measurements of the animal's perimeter, surface area, rotation angle and length are calculated from the animal's top down body view (an example is shown FIG. 1G). Other measurements such as height, width, depth and velocity can be calculated from the animal's depth profile of which an example is shown in FIG. 1H. More complicated measurements, such as spine curvature and limb position require more in-depth calculations, but these calculations can still be performed at the same rate that the video is recorded (typically 24, but up to 100, frames/second).

All of the parameters extracted from the mouse at each point in time constitute a vector, which describes the animal's posture as a point in a high-dimensional "posture space". A single session of an experiment may comprise thousands of these points. For example, a half-hour experiment tracking a single animal, recorded at 24 frames/second, will produce over 40,000 points. If there were only two or three parameters measured per frame, one could visualize the postural state of the animal over the course of the experiment with a 2D scatterplot.

However, since many more points are measured than can be sorted sequentially, and there are many more dimensions than is possible for humans to reason with simultaneously, the full distribution of measured postures cannot be segmented by hand and by eye. So, as described below methods are employed to automatically discover recurring or stereotyped postures. The methods used comprise both dimensionality reduction and clustering techniques, which both segment and model the distribution of postures exhibited in the data.

The clustering process proceeds as follows: First, a great degree of covariance will be present between variables in the dataset, which will confound even highly sophisticated clustering methods. For instance, if a preyed-upon animal's primary way of reducing its visibility is by reducing its height, the animal's height can be expected to tightly covary with its surface area. One or two parallel and complementary approaches are used to remove covariance. For example, since all clustering methods require some notion of distance between points, in one approach, the Mahalanobis distance is used in place of the Euclidean distance that is conventionally used in clustering methods. The Mahalanobis distance takes into account any covariance between different dimensions of the posture space, and appropriately scales dimensions to account more or less importance to different parameters.

In another approach, dimensions may be explicitly combined, subtracted, or eliminated by a suite of dimensionality reduction methods. These methods include principal components analysis (PCA), singular value decomposition (SVD), independent components analysis (ICA), locally linear embedding (LLE) or neural networks. Any of these methods will produce a lower-dimensional representation of the posture space by combining or subtracting different dimensions from each other, which will produce a subset of dimensions that is a more concise description of the posture space. It has been found that dimensionally-reducing a dataset which contains covariance within it ultimately produces better clustering results.

After the data has been prepared for clustering by removing covariance, the data is segmented into clusters using a number of state-of-the-art as well as established clustering algorithms. The performance of the output of each clustering algorithm is quantitatively compared, allowing a rigorous selection of a best cluster set.

Clustering proceeds as follows. First, a suite of unsupervised clustering algorithms is applied. These clustering algorithms can include the K-means method, the vector substitution heuristic, affinity propagation, fuzzy clustering, support vector machines, superparamagnetic clustering and random forests using surrogate synthetic data.

Next, the output of each algorithm is evaluated by taking the median value of two cluster evaluation metrics: the Akaike information criterion (AIC) and the Bayesian Information Criterion (BIC). The AIC and BIC are similar, but complementary metrics of the "goodness-of-fit" for a clustering solution on a dataset. The BIC preferentially rewards simpler clusterings, while AIC will allow solutions with more clusters, but with tighter fits. Using both simultaneously allows a balance to be struck between complexity and completeness. Clustering from the algorithm that produces the solution with highest likelihood, as calculated by the highest median value of the AIC and BIC is used.

When the vectors of these clusters are visualized in three or fewer dimensions, they display as "clusters". An example is shown in FIG. 3 which was produced by an unsupervised clustering of mouse posture data. Extracted postural variables, including length, aspect ratio, height, spine angle and many others were dimensionally reduced to two principle components, PC1 and PC2, which are shown in a scatter plot in FIG. 3. In this plot, stereotyped postures appear as clusters in the principle component space. Each cluster represents a distinct and recognizable posture. For example, the third cluster represents "rearing" and the fifth cluster represents normal walking.

Static behaviors, like a fixed or frozen posture, are an informative, but incomplete description of an animal's behavioral repertoire. The aforementioned clusters represent postures at fixed points in time. However the inventive method also captures how these postures transition between themselves and change. In other words, the invention includes the formation of a quantitative description of the typical and atypical types of movements an animal makes, either unprompted, or in response to stimuli. Typical behaviors would include (but are certainly not limited to) normal modes of walking, running, grooming, and investigation. Atypical movements would include seizure, stereotypy, dystonia, or Parkinsonian gait. This problem is approached in a manner similar to the clustering problem; by using multiple, complementary approaches along with techniques to select the best among the employed models.

The invention also addresses an obvious, but difficult problem for the automated discovery of behaviors: how long does a behavior last? To address this problem a number of methods are deployed in parallel for variable-length behaviors, each with respective strengths and weaknesses.

More specifically, search algorithms are employed that are optimized only for a fixed length behavior, and that ignore any behavior that occurs over timescales that are significantly longer or shorter than the fixed length. This simplifies the problem, and allows the clustering techniques previously employed to be used without modification. Illustratively, the time-series of posture data is scanned in a sliding window, saving vectors in regular intervals, and perform clustering on those saved periods of posture data. Differently-sized behaviors are found simply by varying the size of the sliding window. The longer the window, the longer the behaviors being searched for, and vice-versa.

Extending the previous approach, a search is conducted for fixed-length behaviors, but the search is repeated over a wide spectrum of behavior lengths. While this is a brute force technique, it is feasible and reasonable given the ever-decreasing cost of computing power. Third-party vendors, such as Amazon, offer pay-as-you-go supercomputing clusters (Amazon EC2 provides state-of-the-art servers for less than $2.00/hr, and dozens of them can be linked together with little effort), and the commoditization of massively parallel computation on graphics cards (GPUs) has made supercomputing surprisingly affordable, even on the desktop. More specifically, multiple behavioral lengths are searched for by using a multiplicity of window sizes. The principle of using sliding windows to select techniques reserved for static segments of data on time-evolving data is commonplace. An example of a sliding window technique which is used commonly for audio, but is suitable for use with the present invention is a Welch Periodogram.

Instead of exclusively using the large class of machine learning algorithms that require fixed-dimension data, algorithms that are more flexible are also employed. Hidden Markov Models, Bayes Nets and Restricted Boltzmann Machines (RBMs) have been formulated that have explicit notions of time and causality, and these are incorporated into the inventive method. For example, RBMs can be trained, as has been demonstrated capably in the literature (Mohamed et al., 2010; Taylor et al., 2011), to model high-dimensional time-series containing nonlinear interactions between variables.

Providing plain-language labels for the resulting clusters is a simple matter of presenting recorded video of the animal while it is performing a behavior or exhibits a posture defined by a cluster, and asking a trained observer to provide a label. So, minimal intervention is required to label a "training set" of 3D video with the inventive method, and none is required by the user, because the results of the automatic training are included into the client-side software. As mentioned above, these natural language labels will not be applied to all postural clusters, although all postural clusters are considered behaviorally meaningful.

FIGS. 2A and 2B illustrate how clustering in accordance with the inventive principles indicates overall animal behavioral state changes when an animal is offered odor stimuli. FIG. 2A shows plots of six principle components (PC1-PC6) versus time generated when a mouse was presented with blank, fearful (TMT) and mildly positive odor (Eugenol) treatments for 180 seconds each separated by 10 minute intervals. When the mouse behavior was analyzed, the six principle components were found to capture most of the variance in the mouse posture. In FIGS. 2A and 2B, each vertical line represents a video frame of approximately forty milliseconds.

FIG. 2B shows the data of FIG. 2A clustered in accordance with the principles of the invention irrespective of the odor treatment. It was found that different treatments preferentially elicited different behaviors. The clusters were inspected by trained observers and some were given English language labels.

The only effort by the user to setup the system is to download the software, point the Kinect (or other depth camera) at the experimental area, and plug it in to the computer. All behavioral analysis in the client software occurs on-line, allowing the user to see the outcome of his experiment in real time, instantaneously yielding usable behavioral data. A simple "record" button begins acquisition and analysis of one or more animals recognized in the camera field of view, and the output data can be saved at the end of the experiment in a variety of commonly used formats, including Microsoft Excel and Matlab files. And, because the client-side setup requires only a computer and a Kinect, it is quite portable if the software is installed on a laptop.

In another embodiment, a capacitive touch screen may be used to sense movement of the mouse over the touch screen surface. Physiological aging and a variety of common pathological conditions (ranging from amytrophic lateral sclerosis to arthritis) cause progressive losses in the ability to walk or grasp. These common gait and grasp-related symptoms cause significant reduction in the quality to life, and can precipitate significant morbidity and mortality. Researchers working to find treatments for deteriorating locomotion rely heavily mouse models of disease that recapitulate pathology relevant to human patients. Historically, rodent gait is evaluated with ink and paper. The paws of mice are dipped in ink, and these subjects are coerced to walk in a straight line on a piece of paper. The spatial pattern of the resultant paw prints are then quantitated to reveal abnormalities in stride length or balance. As set forth above, video cameras have automated some aspects of this phenotyping process. Mice can be videotaped walking in a straight line on glass, and their paws can be detected using computer vision algorithms, thus automating the measurement of their gait patterns. However, both of these approaches are unable to continuously monitor gait over periods of time longer than it takes for the mouse to traverse the paper, or field of view of the camera. This type of long-term, unattended monitoring is essential for a rich understanding of the progressive onset of a neurological disease, or of the time course of recovery after treatment with a novel drug.

To enable accurate and long-term gait tracking, the present inventors propose to deploy capacitive touchscreens, like those found in popular consumer electronics devices (such as for example the Apple iPad) to detect mouse paw location and morphology. The use of touchscreens for paw tracking has several advantages over video tracking First, detection of paws is extremely reliable, eliminating the difficult stage of algorithmic detection of the paws in video data. Second, little or no calibration is required, and the mouse may move freely over the surface of the touchscreen without interfering with tracking fidelity. Third, capacitive touchscreens do not erroneously detect mouse detritus as paw locations, a common occurrence that can confound video trackers, which require an unsoiled glass floor for paw detection. Fourth, because the animal can be paw-tracked while moving freely over the whole touchscreen (which are available for immediate purchase as large as 32" diagonal, or as small as 7" diagonal), this input modality can be paired with top-down recording, for example as set forth above, to create a high-resolution behavioral fingerprint of the mouse, which combines conventional metrics, like overall body posture, with gait analysis. This integrative approach is practical with touch technology as the gait sensor.

It is contemplated that touch screen technologies other than capacitive may also be used, such as for example resistive, surface acoustic wave, infrared, dispersive signal technology or acoustic pulse recognition.

The present inventors have developed a system using affordable, widely available hardware and custom software that can fluidly organize and reconfigure a responsive sensory and cognitive environment for the animal. Cognitive tasks are configured to respond to the laboratory animal's feet on a touch-sensitive device, and feedback is given through a dynamic graphic display beneath the animal, on surrounding walls, and via speakers beneath and around the animal. Cognitive tasks, which previously required the physical construction of interaction and sensing devices, can now be created and shaped easily with software, affording nearly limitless sensory and cognitive interaction potential.

Some parameters of animal behavior can be more optimally obtained using a touch-sensitive device. For example, in mice, foot-touch position and time of foot-to-floor contact can be obtained with a touch-sensitive device. These motions are incredibly difficult to reliably extract with conventional cameras, and much easier to accomplish with the use of touch-sensitive surfaces.

The combination of a touch-sensitive device and a depth camera make the extraction of all parameters more reliable. Also, building a full 3D model of an animal, such as a mouse, including all limbs, requires multiple perspectives, which can be accomplished with a depth camera and a touch-sensitive surface.

Further, when used as the floor of the animal's home cage, a touch-sensitive surface allows 24-hour gait monitoring for high-density phenotyping of subtle or developing movement disorders.

Last, touch-sensitive technology can bolster the resolution of video-based behavioral phenotyping approaches. Specifically, when combined with 2D or 3D cameras above or to the side of the animal, adding the position of the animal's feet on a touchscreen greatly specifies the current pose the animal is exhibiting. Much higher accuracy behavioral tracking is possible with the addition of this touch information.

This invention includes 4 key components: (1) The real-time acquisition of touch location and velocity from a touch-sensitive device, such as a capacitive touchscreen or pressure mapping array. (2) Positive assignment of touchpoints to the body parts of each one of possibly many animals, possibly with the aid of an overhead or side camera system. (3) Processing of this touch information to reveal additional parameters, possibly with the aid of an overhead or side camera system. This may include, e.g., if the animal is headfixed, his intended velocity or heading in a virtual reality environment, or in a freely moving animal, the assignment of some postural state, such as "freezing" or "rearing". (4) Visual, auditory or nutritive feedback, using the extracted touchpoints and additional parameters, into an external speaker and the display of a touchscreen, or of an LCD laid under a force-sensitive pressure array. This feedback may be, e.g., a video game the mouse is playing using its feet as the controller, a food reward from an external food dispenser the animal gains from playing the video game well, a visual pattern used to probe the mouse's neural representation of physical space, or an auditory cue increasing in volume as he nears closer to some invisible foraging target.

Taken together, items 1-4 constitute an invention for providing an animal with a closed-loop, highly-immersive, highly-controlled sensory and cognitive environment. Additionally, the system provides an experimenter with a detailed description of the mouse's behavioral participation in the environment. The construction of the device first requires a touch-sensitive device that can track multiple touchpoints simultaneously. Capacitive touchscreens, like those in the Apple iPad or 3M Multitouch displays are appropriate, as well as thin pressure-sensitive pads, like those constructed by Tekscan, as well as Frustrated Total Internal Reflectance touch surfaces. Touchscreens are preferable, but not required, because they include a built-in visual display for easy and programmable feedback. The touch surface is set as the floor of the animal's arena. All touch-surface vendors supply simple software APIs to query and receive high temporal and spatial resolution touch positions. The present inventors then take these provided touch points, and using simple heuristics, assign individual touches to floor-contacting body parts of a laboratory animal, like the paws, and occasionally tail and nose. If the present inventors have an additional video stream, the present inventors may combine the position of the floor-contacting body parts with a top-down or side-on 2D or depth camera view to further enrich knowledge of the animal's posture, body kinematics or intention.

The sub-second configuration of the animal's floor-contacting anatomy serves as the input "controller" to any number of possible software programs realizable in the system of the present invention. The mouse, for instance, may play a video game, where he has to avoid certain patterns of shapes on the visual display, and is punished for failing to do so with a loud unpleasant noise, or rewarded for succeeding with the automated delivery of a small food reward. Since touch sensing technology has a very low latency (commonly less than five milliseconds), numerous operant behavioral neuroscientific apparatuses can be recapitulated on a single device, and an experimenter can switch between them as easily as one would launch separate apps on the iPhone. If capacitive touchscreens are used, they may be cleaned easily, and do not produce spurious or noisy data when laboratory animal detritus is placed upon them, allowing for continuous, fluid and flexible 24-hour cognitive and sensory testing. The ability to place points-of-interest anywhere on the touchscreen during a cognitive task allows for new types of tasks to employed. Free-ranging foraging behaviors are exceptionally difficult to study in a laboratory setting, because they require a changing and reconfigurable environment on the timescale of seconds or minutes. The effective combination of display and touch technology allows the facile interrogation of complex and significant innate search behaviors that is not achievable with available behavioral operant technology.

With positive identification of the animal's feet, and removal of spurious touches from the animal's nose, tail and genitalia, the touch system becomes a powerful automated gait tracker. Existing gait tracking systems use 2D cameras and transparent floors, paired with simple blob-detection algorithms to detect feet. These approaches suffer several key limitations the system of the present invention addresses. First, existing gait tracking requires a clear bottom-up view that can be quickly occluded by detritus. Through either the touch-sensing mechanism or software algorithms, touch-screens are insensitive to moderate amounts of animal waste, making their use feasible in the home cage of the animal. Second, existing gait tracking systems require the animal to move along a relatively short linear track. The touch system of the present invention allows the animal to roam freely. Last, experimenter supervision is required for the operation of existing gait tracking systems. The presence of a human in the experiment room can be a serious confound for more sensitive animal studies involving e.g., anxiety or pain. Touch-screen systems, when used as the floor of an animal's home cage, require comparatively little intervention and upkeep, and thus allow continued observation of the gait of an undisturbed animal.

The animal may be head-fixed above a touch-sensitive surface, and a virtual reality system may be set up in front, below, and around the animal. In this realization, the touchscreen serves as a sensitive input device for a behavior virtual reality system. These systems traditionally use an air-suspended styrofoam ball as the locomotor input for the VR system. The styrofoam ball is initially difficult for the animal to control, and even with increased dexterity through training, the inertia of the ball limits the precision with which the animal may move through the VR environment. With a touch-screen collecting locomotor input, the animal may start and stop motion through the VR environment as fast as it can control its own body. Additionally, turning in place and about-face maneuvers are impossible on the ball system, but are essential movements in the mouse's behavioral repertoire. The touchscreen in a VR system may thus allow new flexibility and precision in head-fixed VR behavioral studies.

In addition to touch-sensitive devices, the present invention can incorporate frustrated-total-internal-reflectance (FTIR) sensing. The FTIR technology requires a separate projector to provide visual feedback, but can be fully integrated.

Part Two: Quantitative Phenotyping of Behaviors in Animals Including Social and Odor-Driven Behaviors in ASD Mice Improving Methods for Data Acquisition The underlying motivation for the present invention arises from the lack of comprehensive quantitative metrics that capture the behavioral repertoire (including normal home cage behaviors, social behaviors, and odor-driven behaviors) of mice. The absence of dense behavioral data impedes both rigorous tests of the face validity of ASD disease models, and basic research into the structure and function of neural circuits underlying ASD-relevant behaviors (which themselves are certain to be substrates of disease). Current approaches to behavioral analysis have been well reviewed, but in the context of the present invention there is value in briefly considering how researchers typically approach this problem. Acquisition of behavioral data typically takes place either in the home cage or in arenas with defined architectures designed to elicit various behaviors (such as anxiety in the case of the open field or elevated T maze, choice behaviors in the case of a Y maze, social behaviors in a three compartment assay, and the like) [8][9][18]. Traditional beam-crossing metrics have largely been supplanted by data acquisition using single digital video cameras capable of generating high fidelity representations of the experiment in two-dimensions; because many behavioral apparatuses are organized in the XY axis (and have opaque walls), these cameras are placed overhead and the disposition of the animal is recorded over time. In certain cases, such as during analysis of home cage behavior, data is acquired from two cameras, one with a birds-eye view and the other recording from the side, thereby enabling researchers to view two orthogonal mouse silhouettes [19][20]. However this approach has significant limitations: one can only record in this manner in apparatuses in which all sides are clear and in which there is no interior plastic orthogonal to the side-view camera, and current software implementations do not register the two video feeds to generate true depth data. As such this method can only be deployed in contexts where the expected behaviors are spatially isotropic and normally expressed in clear behavioral boxes (like modified home cages).

FIGS. 4A-4E depict the assessment of odor-driven innate behaviors in two and three dimensions. A conventional two-compartment behavioral choice assay (FIGS. 4A and 4B) reveals that mice exhibit robust innate behavioral attraction to female urine and eugenol, and avoidance to putative predator odors (TMT, MMB), aversive pheromones (2-heptanone and 2,5-DMP) and spoiled food odors (butyric acid). Odors are soaked into filter papers, which are placed in the small compartment of a cage divided by a parafilm curtain. This assay suffers from incomplete control of gas-phase odorant concentration, poorly defined spatial odor gradients and experimental variability due to the physical interaction of the animal with the odor source. The present inventors have therefore developed a new behavioral arena (FIG. 4C, left), in which odors are delivered to each of 4 corners in gas phase via high-performance computer-controlled Teflon valves. Use of custom-written Matlab code to track animal trajectories (FIG. 4C, right, animal position shown with a line) reveals that mice explore each compartment of this apparatus equally during a control experiment in which air is blown into each of the four corners. Delivering the fox odor TMT in the upper right corner causes qualitative (FIG. 4D, left) and quantitative (FIG. 4D, right) avoidance behaviors that are extraordinarily robust and well controlled. (FIG. 4E) Re-imaging the apparatus shown in (FIG. 4C) using a depth camera, and plotting aspect ratio versus height (with time heatmapped) reveals that under control conditions mice stay stretched and low to the ground (FIG. 4E, left) consistent with normal exploratory behaviors, but when confronted with a salient odor like TMT become compressed (from the perspective of the overhead camera) and elevate their noses (FIG. 4E, right), consistent with sniffing events (black arrow). These data reveal that odor stimuli alter the overall behavioral program of the animal (rather than merely altering the animal's position).

Figure 4A:
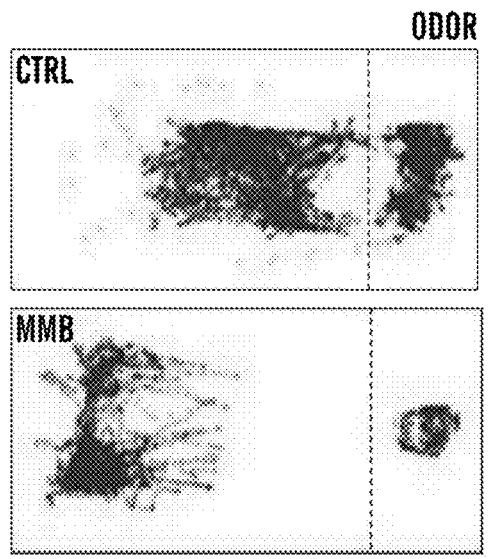
FIGS. 4A-4E depict assessment of odor-driven innate behaviors in two and three dimensions.
Figure 4B:
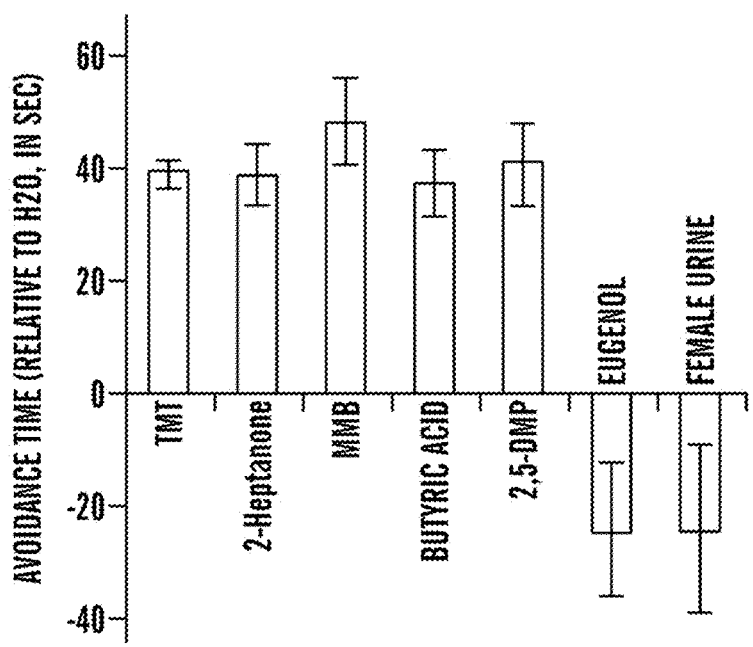

While there are a number of metrics that can be used to quantify morphological data captured by two-dimensional images (ranging from spatial position to horizontal spine curvature), nearly all meaningful mouse behavior—both in ethological and laboratory contexts—takes place in three dimensions. Consider a simple and typical experiment in which researchers introduce an odor-soaked filter paper to an animal housed in a cage, and assess whether the animal considers the odorant attractive or aversive [21][22] Two-dimensional spatial data captured from an overhead camera can be plotted to reveal whether a given odorant causes a change in the average position of the animal (FIG. 4A-4B). By modifying this arena and using improved cameras the present inventors can obtain more rigorous measurements of how a given odor will alter the average distribution in space of an animal (FIGS. 4C-4D), and then use this data to generate a unidimensional measure of attraction or avoidance (as shown for the aversive odor TMT, FIG. 4D). However, if the present inventors take into account how the animal is behaving in the third dimension, it becomes clear this metric for measuring avoidance significantly understates the overall consequence for the animal of interacting with an aversive sensory stimulus like TMT. For example, graphing the aspect ratio (i.e., how stretched out or compressed the animal appears when imaged from above) on the ordinate and head position of the mouse in Z on the abscissa reveals that exposure to an aversive odorant causes the animal to change his posture from one in which he is stretched out and near the ground (as would be expected for free exploration) to one in which his aspect ratio condenses and his head rises (as would be expected during sniffing behaviors)(FIG. 4E). This revealed sniffing behavior would be difficult or impossible to identify from data limited to two dimensions (as it cannot be disambiguated from any other posture that compresses the aspect ratio). Thus the presentation of a stimulus does not simply cause a change in the position of the animal over time (as would be typically assessed and shown as FIG. 4A), but rather induces a wholesale change in the behavioral state of the animal, one which is best assessed in three dimensions instead of two.

However, as mentioned above, currently implemented approaches for capturing data in three dimensions do not extract true depth data and are generally limited to those in which two cameras can be aimed in orthogonal axes onto clear behavioral apparatuses like modified home cages [19] [20], and thus cannot be used in many of the standard behavioral arenas deployed to assess ASD model mice (including the open field, T and Y-mazes and three compartment social behavior apparatuses) [8][9][23]. To address this limitation the present inventors record mouse behavior using depth cameras. One common depth camera design enables stereoscopic data acquisition from a single vantage point by taking advantage of structured illumination and basic rangefinding principles; the alternative Time-of-Flight design uses high-precision measurements of time differences between the arrival of laser pulses to capture depth information. Although depth cameras have been deployed by one group to track the trajectories of rats in a clear box [24], these cameras have not yet been used to extract high-resolution morphometric data for behavioral classification. Because depth cameras can calculate Z position while imaging from a single viewpoint, the use of this imaging approach makes it possible to explore the three dimensional disposition of a rodent in nearly any behavioral apparatus. The present inventors' laboratory has successfully established protocols to use depth cameras to track mice in their home cage, in the open field, in the standard three compartment assay for social interactions and in a new innate olfactory assessment arena (FIGS. 5A-5H, 6 and 7).

FIGS. 5A-5H generally relate to the use of depth cameras to acquire and segment 3D video data of mouse behavior. (FIG. 5A) To effectively distinguish the 3D image of a mouse from the background of the behavioral arena, a baseline image is captured, calculated as the median value of 30 seconds of imaging of an animal-free behavioral arena (here shown using the odor quadrant arena described in FIG. 4C). (FIG. 5B) Images are continuously acquired during the experiment while an animal explores the apparatus. (FIG. 5C) The baseline image in (FIG. 5A) is subtracted from the acquired depth image in (FIG. 5B) to reveal a noisy difference image. (FIG. 5D) Median filtering denoises these subtracted images. (FIG. 5E) Contours are then outlined using a detection algorithm after taking thresholds that distinguish figure from ground. (FIG. 5F) The 3D image of a mouse is extracted using the derived contours; height data in this figure is heatmapped (red=more vertical). (FIG. 5G) Parameters of the mouse's top-down view are easily derived from this dataset, including perimeter, area, rotation angles and length (black lines). (FIG. 5H) Using the depth profile of the mouse, spine curvature and height are also easily calculated (black lines).

Figure 6:
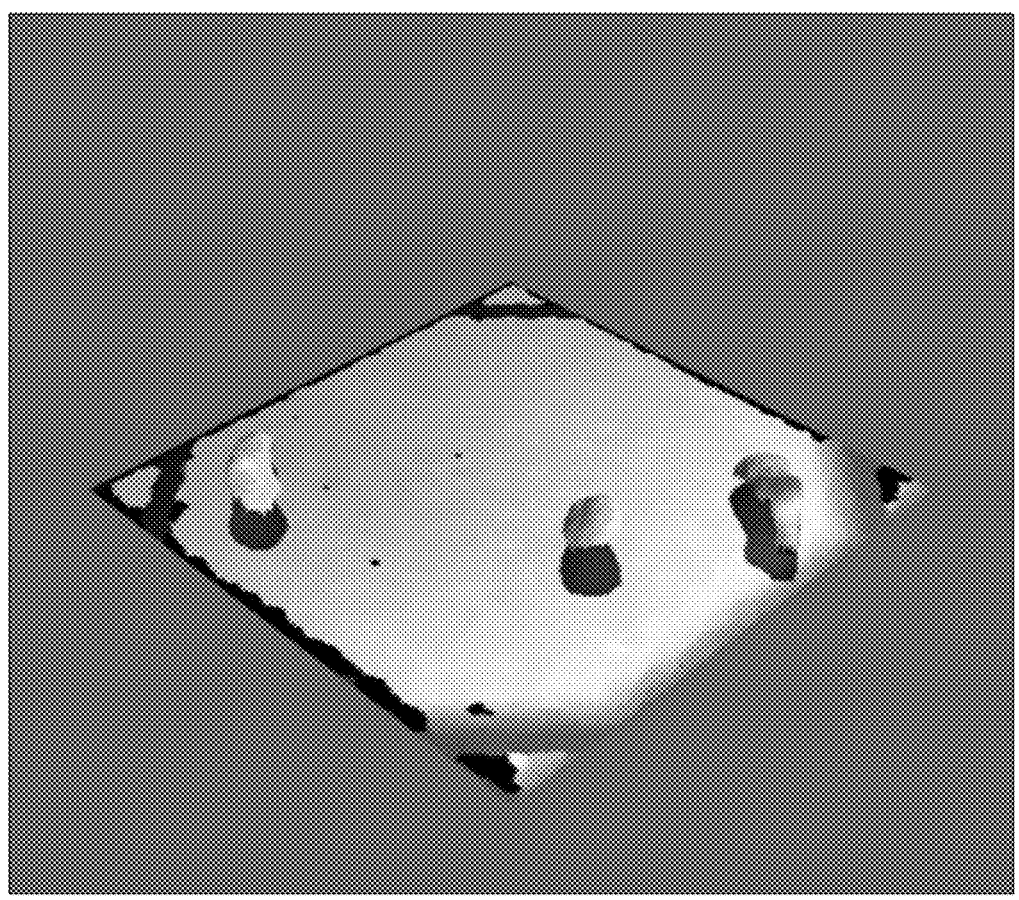
FIG. 6 depicts the tracking of behavior of a single mouse in 3D over time.

FIG. 6 depicts the tracking of behavior of a single mouse in 3D over time. A single mouse, at three different points in time, behaving in the odor response arena shown in FIGS. 4A-4E. The background image of the apparatus is included in grey to aid in orientation, and shadows added to emphasize depth. Heights of this imaged mouse are heatmapped (red=vertical height). Note that at these three times the animal exhibits quite distinct postures.

Figure 7:
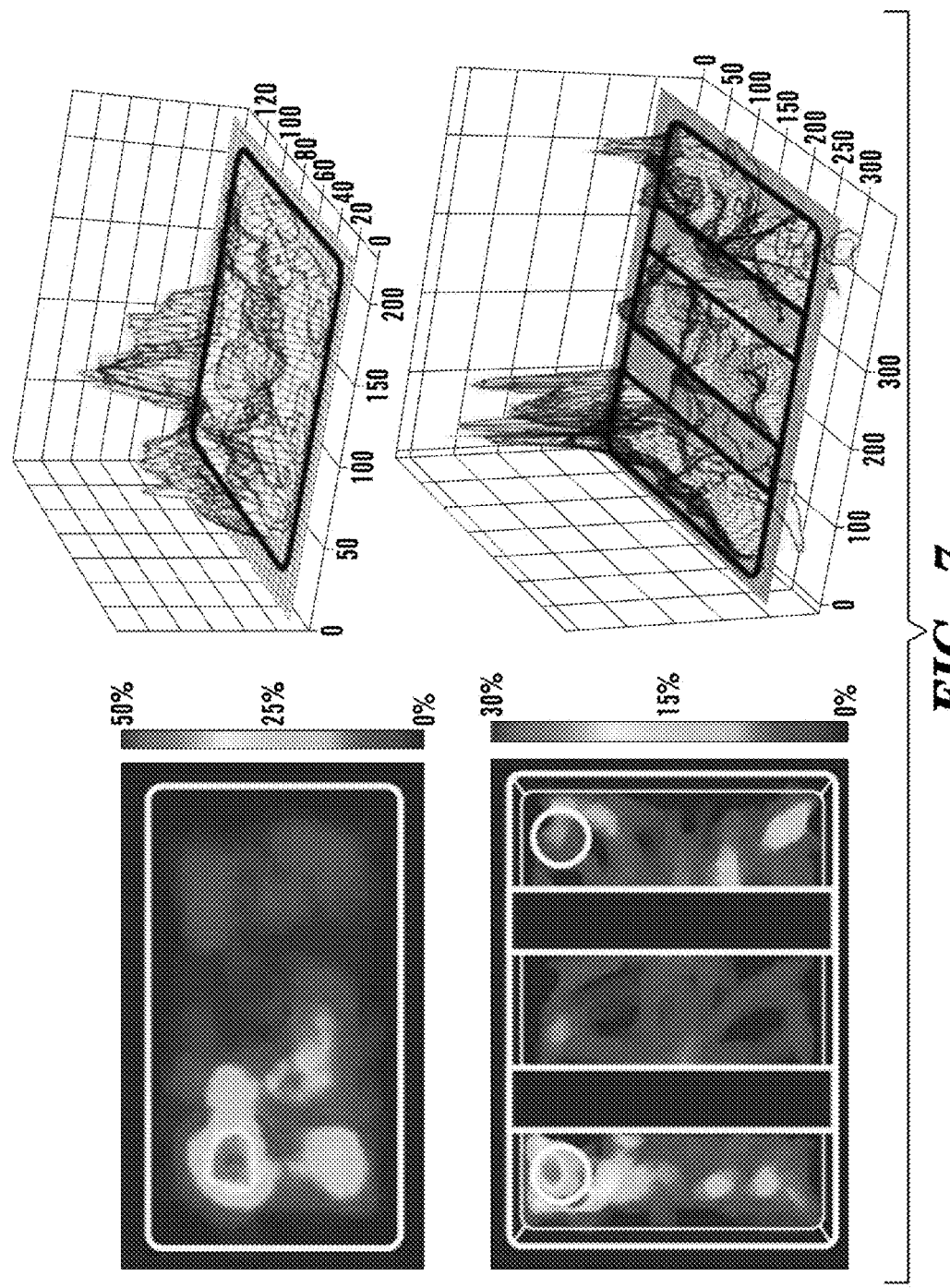
FIG. 7 depicts tracking multidimensional spatial profiles in the home cage and during a three chamber social interaction assay. Average occupancy is heatmapped for a single mouse in a homecage over 30 minutes (FIG. 7, upper left), and overall distribution in height in Z is plotted for comparison (FIG. 7, upper right). During a social interaction test (FIG. 7, lower left), an individual mouse spends much more time interacting with a novel conspecific (in left compartment, FIG. 7, at upper left) than with the novel inanimate object control (in right compartment, FIG. 7, upper right). Note that when the data are plotted in Z (FIG. 7, lower right) it is clear that the test mouse extends his Z-position upwards.

FIG. 7 generally relates to tracking multidimensional spatial profiles in the home cage and during a three chamber social interaction assay. Average occupancy is heatmapped for a single mouse in a homecage over 30 minutes (FIG. 7, upper left), and overall distribution in height in Z is plotted for comparison (FIG. 7, upper right). During a social interaction test (FIG. 7, lower left), an individual mouse spends much more time interacting with a novel conspecific (in left compartment, FIG. 7, at upper left) than with the novel inanimate object control (in right compartment, FIG. 7, upper right). Note that when the data are plotted in Z (FIG. 7, lower right) it is clear that the test mouse extends his Z-position upwards; this posture is consistent with sniffing behaviors (which can be directly demonstrated both by video review and by QBP analysis, see FIGS. 8, 9A-9B, 10 and 11).

The present inventors have written custom software that enables efficient segmentation of the mouse from any given background (and which works with depth camera data under nearly all lighting conditions and for all combinations tested of coat color and background color, obviating the need for specific lighting or painting/marking of the animal), and can use this code to extract all of the unsupervised behavioral parameters traditionally generated by 2D cameras (FIGS. 5A-5H, Table 1). In addition, because the data output from a depth camera includes the third dimension, a large number of higher-order morphometric parameters can be generated (Table 1).

TABLE 1

MORPHOMETRIC PARAMETERS EXTRACTED FROM DEPTH CAMERA DATA (NOTE: PARAMETER LIST INCLUDES INTERACTIVE METRICS)

1. Head direction
2. Heading towards predefined area (based on head direction)
3. Head angle relative to predefined point
4. Velocity during transition between predefined areas (based on contour outline)
5. Time of transition between predefined areas (based on contour outline)
6. Distance to predefined area (both centroid and minimum distance based on outlined contour)
7. Position in predefined areas (both centroid and percent occupancy based on full body contour)
8. outline)
9. position (both x, y centroid and full contour outline)
10. contour area
11. contour perimeter
12. contour tortuosity
13. contour eccentricity
14. best-fit ellipse
15. periodic B-spline approximation of horizontal outline
16. first, second, and third derivatives of periodic B-spline approximation of horizontal outline with
17. respect to single B-spline parameter
18. bivariate B-spline approximation of 3d contour
19. first, second and third derivatives of bivariate B-spline approximation of 3d contour with respect
20. to both b-spline parameters.
21. maximum height
22. volume

TABLE 1-continued

MORPHOMETRIC PARAMETERS EXTRACTED FROM
DEPTH CAMERA DATA (NOTE: PARAMETER LIST
INCLUDES INTERACTIVE METRICS)

23. velocity
24. acceleration
25. angular velocity
26. angular acceleration
27. head angle (approximate)
28. spine outline in horizontal dimension
29. first and second derivatives of spine outline
30. spine outline in vertical dimension
31. first and second derivatives of spine outline
32. raw body range image, cropped, aligned, and rotated
33. first and second derivatives of mouse full body range image with respect to time
34. Velocity towards other animal
35. Acceleration towards other animal
36. Distance from other animal
37. Head direction relative to other animal's tail base
38. Head direction relative to other animal's head
39. Distance from head to other animal's head
40. Distance from head to other animal's tail base
41. Correlation of animal's velocity vector with another animal (moving together, e.g. pursuit)

This dataset can therefore be used to calculate (in an unsupervised manner) both basic statistics, such as average velocity, and previously inaccessible metrics, such as spine curvature in Z. The multidimensional data set obtained via depth cameras therefore provides a much richer substrate for subsequent statistical analysis than can be generated using typical 2D cameras.

Improving Methods for Data Analysis

Current methods for data handling after video acquisition varies, but nearly always involves either direct or indirect human intervention. Classification of animal behavior is often achieved by human observers who view the video stream (either in real time or after the experiment is completed) and identify various behaviors using natural language terms such as "running" or "eating" or "investigating" [8] [25]. More sophisticated, commercially-available behavioral analysis software enables users to define which combinations of observed morphometric variables correspond to a behavioral state of interest, whose dynamics are then reported back to the user [26][27]. Other algorithms extract morphological parameters from the video data and then compare these datasets to large hand-curated databases that correlate a particular set of mathematical parameters with their likely natural language descriptors [28]. Recently developed methods search for mathematical relationships amongst tracked behavioral parameters, in order to better define both baseline behavioral states and the alteration of these states by exogenous stimuli or genetic/pharmacological manipulations [19] [28][29][30][31]; however, often even these advanced methods take as their inputs processed data that has been chunked or classified, in some manner, through direct or indirect human intervention.

In many cases the set of currently available analytical methods, despite the persistent influence of human observers, is sufficiently accurate to quantitate those specific behaviors in which a researcher has interest. However, these approaches all essentially depend upon humans deciding, before the experiment, both what constitutes an interesting behavior and how that behavior is defined. In addition to the potential for simple inaccuracy (i.e., the reviewer of the tape mistaking normal grooming for pathological itching), the defining of behaviors a priori comes at two costs. First, as was formalized by Tinbergen [32] (and appreciated well before him), complex behaviors are comprised of sub-states, and distinctions amongst these sub-states are lost when humans chunk together complex motor sequences and assign them natural language descriptors. Subtle and behaviorally-relevant differences in gait, for example, are lost if all that is scored is the time an animal spends running, but can be captured if the states that comprise running (i.e., the rates and degree of flexion and extension at both the hip, knee and ankle joints, and their relationship to translation in all three axes) are characterized. Second, by defining before the experiment occurs what constitutes an important behavior, researchers necessarily exclude from analysis all those behavioral states in which an animal may be engaged in a meaningful behavior that lacks a natural language descriptor. Animal behavior is generally scored, in other words, from an anthropomorphic perspective (i.e., what the present inventors think the animal is doing) rather than from the perspective of the animal [33]. Thus the nearly-ubiquitous interposition of humans into the behavioral analysis process, while seemingly benign and expedient, has limited the resolution with which the present inventors can compare behavioral states, preventing the complete characterization and face validation of ASD models.

Figure 8:
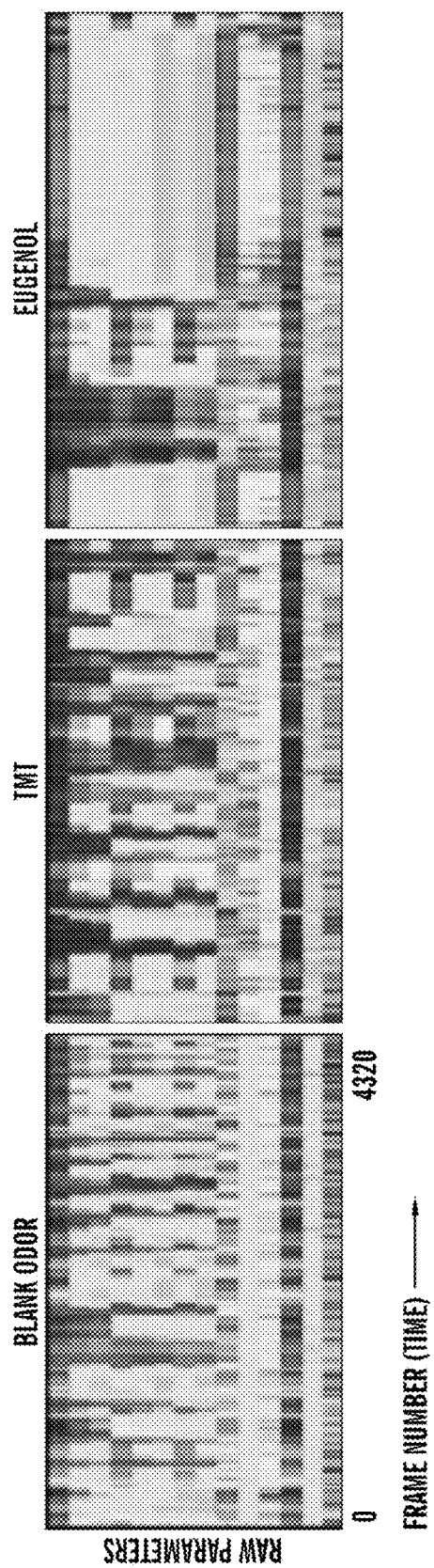
FIG. 8 depicts quantitative behavioral primitives revealed by parameter heatmapping. Raw parameters were extracted from a single mouse behaving in the odor quadrant assay in response to a control odorant (FIG. 8, left), an aversive odorant (FIG. 8, middle) and an attractive odorant (FIG. 8, right) using a depth camera.
Figure 9A:
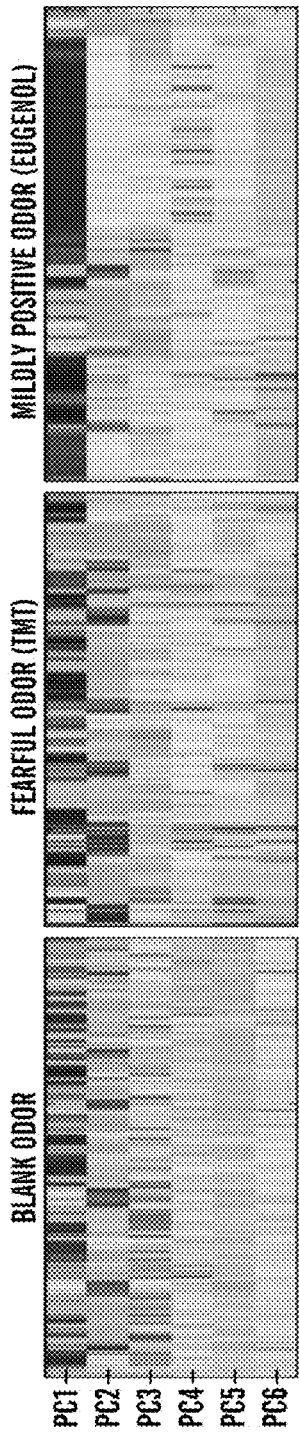
FIGS. 9A-9B depict classification of animal behavior via cluster analysis.
Figure 9B:
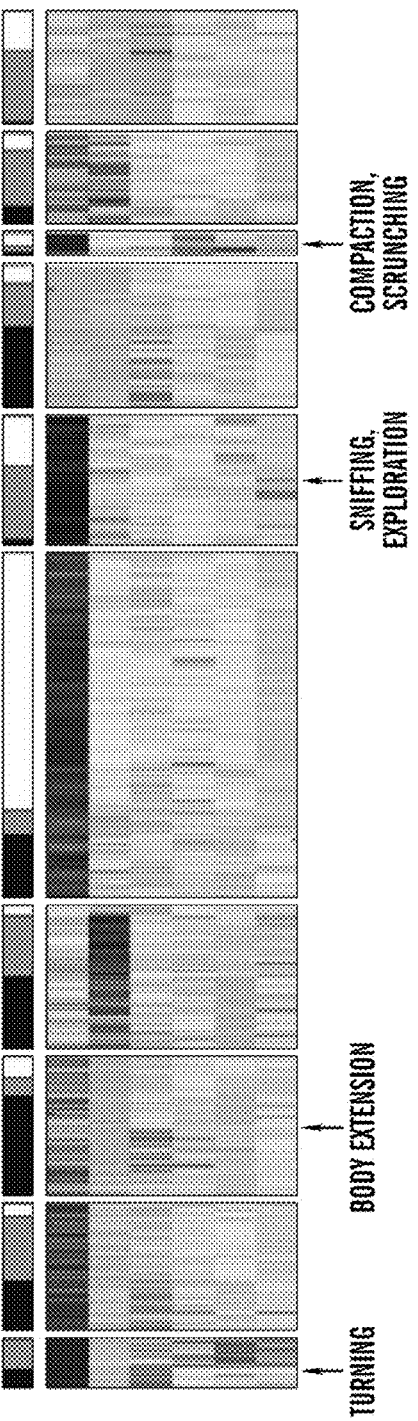

To address this issue the present inventors have developed methods to characterize and quantitate mouse behavior without defining, a priori, which patterns of motor output constitute relevant behaviors. This approach is guided by the present inventors' preliminary data (FIGS. 8, 9A-9B and 10), which suggests that the rich parametric data the present inventors collect via range cameras is both sufficient to describe the morphology of the mouse at any point in time and can be used to classify behavioral patterns without bias. For example, imaging an animal with a range camera at 24 fps and heatmapping the resulting parameters on a frame-by-frame basis reveals that these parameters do not smoothly vary over time, but instead form mathematical clusters (FIGS. 8 and 9A-9B). As time proceeds, and the animal initiates various behaviors, these clusters abruptly transition from one to another. The present inventors term these clusters QBPs (quantitative behavioral primitives, FIGS. 9A-9B depict), and hypothesize that these QBPs represent either behavioral sub-states or, in some cases, behaviors themselves.

FIGS. 9A-9B generally relate to classification of animal behavior via cluster analysis. (FIG. 9A) Raw parameter data from FIG. 8 was subject to PCA, and six principal components were found to account for most of the variance in posture (each frame is approximately 40 ms, capture rate 24 fps, data is heatmapped). (FIG. 9B) The behavior of the mouse was clustered using K-means clustering (independent of stimulus), and different treatments were found to preferentially elicit different behaviors (white, grey and black bars above). Post hoc inspection of the source videotape reveals natural language descriptors for a number of the clusters. Because each of these clusters defines either a behavior or a behavioral sub-state, the present inventors term each of these clusters Quantitative Behavioral Primitives, and analysis using these methods QBP analysis.

To objectively identify and characterize these QBPs, the high-dimensional behavioral data is subjected to standard dimensional reduction techniques including Principal Components Analysis (PCA) followed by K-Means clustering. By subjecting the dataset shown in FIG. 8 to this approach, the present inventors can define 6 principal components that fall into 10 major clusters (the number of which is determined by heuristics determining "goodness-of-fit" for a particular cluster configuration).

FIG. 8 generally relates to quantitative behavioral primitives revealed by parameter heatmapping. Raw parameters were extracted from a single mouse behaving in the odor quadrant assay in response to a control odorant (FIG. 8, left), an aversive odorant (FIG. 8, middle) and an attractive odorant (FIG. 8, right) using a depth camera. By heatmapping these variables over time (at 24 fps), it is evident by inspection that mice do not exhibit smooth transitions between mathematically-described behavioral states, but that these states form visually-identifiable clusters. It is also apparent that the time spent in any given cluster/state, and the transitions between these states is altered as a consequence of interacting with stimuli that cause different behavioral responses.

By unmixing the frames that comprise each cluster and re-ordering the data so that the frames that originated from any given trial are segregated within each cluster (i.e., control, TMT or eugenol), it is clear both that the animal spends some time within all of the QBPs regardless of the stimulus provided and that the amount of time the animal spends within any given QBP varies depending on the encountered stimulus (FIGS. 9A-9B). In addition, the presentation of an odorant alters the probability matrix governing how a subject mouse transitions from one QBP to another (FIG. 11); in other words, the present inventors can use QBP analysis to track the dynamics of mouse behavior, and to ask how changes in stimuli or genotype alter these dynamics.

Figure 10:
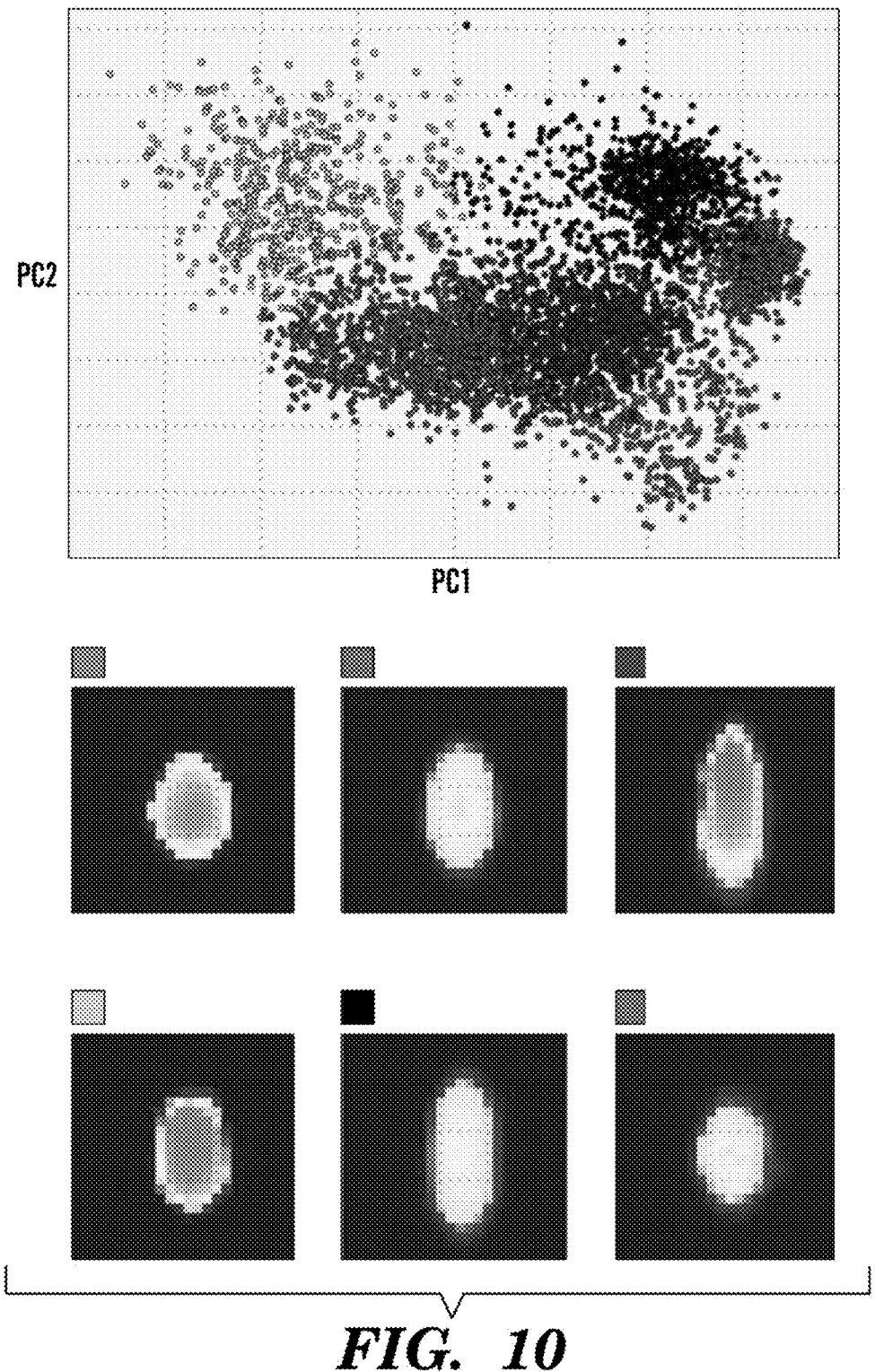
FIG. 10 depicts unsupervised clustering of mouse morphometric data revealing stereotyped mouse postures. By dimensional reduction of extracted morphometric parameters taken from an odor quadrant assay experiment into two principal components, six clusters appear in principal components space (FIG. 10, upper panel). Lower panels depict difference maps from the average mouse position. Review of the source video revealed that each of these postures has a natural language descriptor, including forelimb rearing (i.e., putting paws up on the side of the box, FIG. 10, third lower panel), hindlimb rearing (i.e., nose up in the air, FIG. 10, fourth lower panel), grooming (FIG. 10, first lower panel), walking or slow movement (FIG. 10, second lower panel), running or fast movement (FIG. 10, fifth lower panel), and idle (FIG. 10, sixth lower panel).
Figure 11:
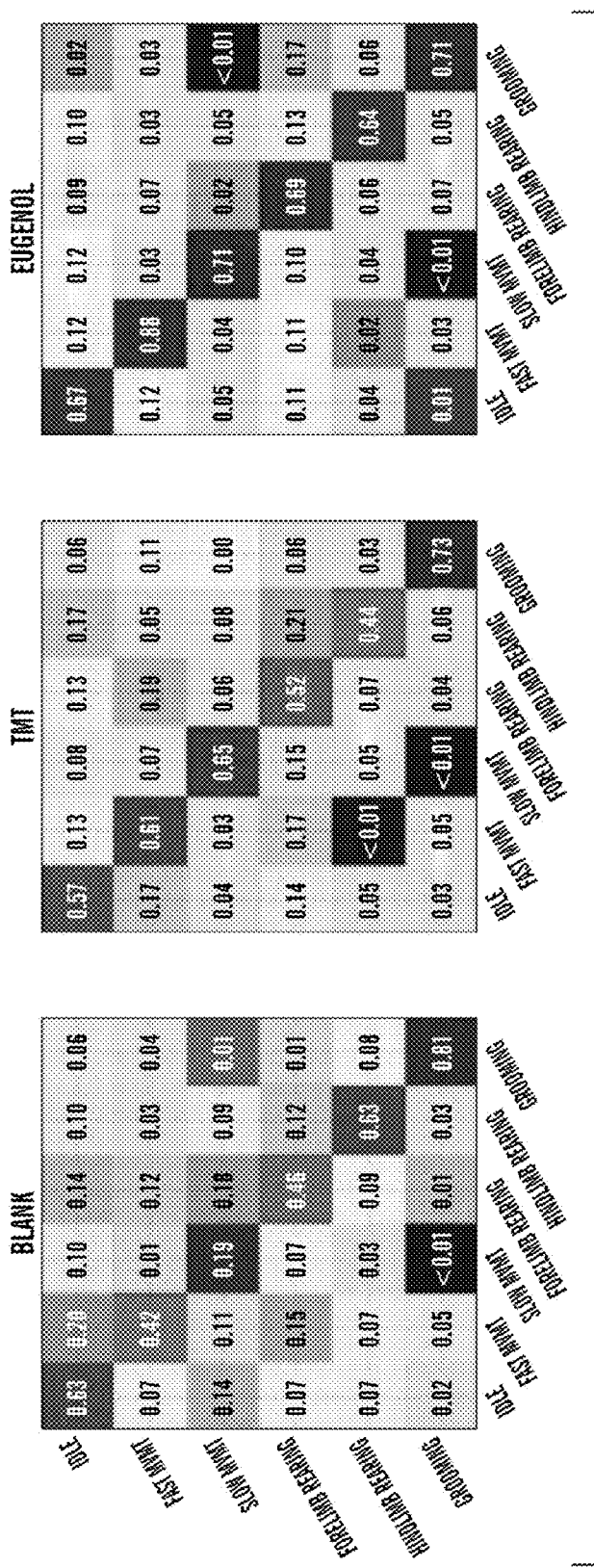
FIG. 11 depicts a matrix of results relating to odors altering QBP dynamics.

FIG. 11 generally relates to odors altering QBP dynamics. FIG. 10 includes a transition matrix plotting the probability of transitions between behavioral states (from the dataset shown in FIG. 10); the likelihood that the state in the column occurs after the state in the row is plotted, with the log probabilities within each square heatmapped.

Taken together, these data are consistent with the present inventors' hypothesis that QBPs represent meaningful behavioral sub-states. The present inventors' QBP-based analytical methods, therefore, enable us to characterize the overall behavioral state of the animal and to describe how this state is altered by differences in stimulus or genotype without direct reference to natural language descriptors. Interestingly, in many cases, when the present inventors view the source video that defines any given QBP cluster, the present inventors can effectively describe the behavior that has been mathematically captured in an unbiased manner by the QBP analysis using traditional descriptors (such as "rearing," "running," "sniffing," and the like). The fraction of QBPs the present inventors can label with natural language descriptors inversely scales with the number of clusters the present inventors allow to be carried forward into the analysis; for example, if the present inventors limit the number of clusters in the specific experiment shown in FIG. 10 to six, the present inventors can assign each a descriptor based upon videotape review.

FIG. 10 generally relates to unsupervised clustering of mouse morphometric data reveals stereotyped mouse postures. By dimensional reduction of extracted morphometric parameters taken from an odor quadrant assay experiment into two principal components, six clusters appear in principal components space (FIG. 10, upper panel). Lower panels depict difference maps from the average mouse position; these maps reveal different average mouse morphologies within each cluster. Review of the source video revealed that each of these postures has a natural language descriptor, including forelimb rearing (i.e., putting paws up on the side of the box, FIG. 10, third lower panel), hindlimb rearing (i.e., nose up in the air, FIG. 10, fourth lower panel), grooming (FIG. 10, first lower panel), walking or slow movement (FIG. 10, second lower panel), running or fast movement (FIG. 10, fifth lower panel), and idle (FIG. 10, sixth lower panel). Both the principal component plot (FIG. 10, upper panel) and the difference map (FIG. 10, lower panels) are color coded.

This observation is consistent with the notion that "chunking" the data via natural language descriptors likely discards behavioral sub-states that may be important from the point of view of the animal, and demonstrates that the present inventors can tune the analysis of the present invention (through alterations in dimensional reduction and clustering approaches) to capture behaviors at various effective resolutions.

Olfaction: A Key Window into Social Behaviors in Mouse ASD Models

Olfaction is the main mechanism used by rodents to interact with their environment; in mice, appropriate behavioral responses to food, predators and conspecifics all depend largely on olfactory function [10][11][12][13][14][15]. Genetic or lesion-based perturbations of the olfactory system cause defects in many of the behaviors affected in mouse models for ASDs, including maternal-pup interactions, social interactions and mating behaviors [13][15][34][35][36][37][38][39]. Under ideal circumstances, detailed assessment of innate behavioral responses to monomolecular odorants derived from socially and environmentally-relevant sources (including foodstuffs, predators and conspecific urines) would be performed to test the integrity of olfactory circuitry in ASD models. However detailed assessment of the olfactory system is almost never performed in this context; typically researchers perform "find the cookie"-style experiments to demonstrate that the olfactory system is grossly normal [9][40]. Recently a more standardized experimental protocol has been developed to assess innate behavioral responses to odorants (similar to FIG. 4A-4B) [21][22]. In this assay, researchers place a mouse within a cage and confront the animal with an odor-soaked filter paper placed on one side of the cage. The animal is tracked by overhead video camera, and the position of the animal is plotted over time, allowing a metric to be calculated that measure the aversiveness or attractiveness of the odor relative to water. However, both this assay and the "find-the-cookie" assay have a number of important flaws: animals can physically interact with the point-source of odorant, which both can cause contamination and prevents the clear identification of the behavioral effect as being mediated by the main olfactory system (as opposed to the vomeronasal or taste systems, both of which report the presence soluble small molecules detected through physical contact). In addition, odorant concentrations at any given spatial location within the arena is not defined, it is not clear whether meaningful odor gradients are established, and mice often ignore new olfactory stimuli presented in this manner, causing wide variability in behavioral responses at the population level.

Figure 12:
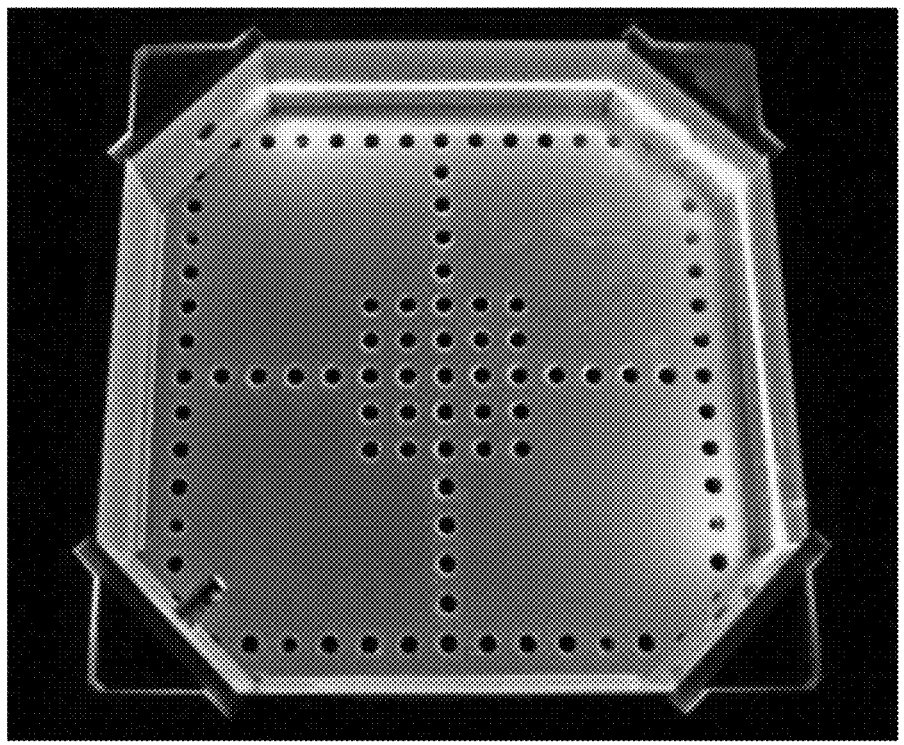
FIG. 12 depicts an odor quadrant assay.

To address these issues the present inventors have developed a novel quadrant assay to assess the behavioral response exhibited by mice to odors delivered in gas phase (FIG. 4C-4E, FIG. 6). Odors are delivered to one of four quadrants via computer-controlled olfactometers, which can deliver precisely timed pulses or square waves of odorants at defined concentrations. These odors are strictly limited to the quadrant in which they are delivered by vacuum ports in the floor of the apparatus; the present inventors have verified the specificity of odor delivery both through the use of mist (visualized by HeNe lasers), and through the use of photo-ionization detectors (FIG. 12). FIG. 12 generally relates to validation of quadrant-specific odor delivery in an odor quadrant assay. Aerosolized mist was delivered to the upper right quadrant at high flow rates, and visualized using a HeNe laser within the quadrant apparatus; the mist is clearly visible at the upper right, and stays localized to that quadrant. Quantitative measurements of odor concentration made with a photoionization device also demonstrate the quadrant-specificity of odor delivery in this apparatus.

Figures 13A, 13B:
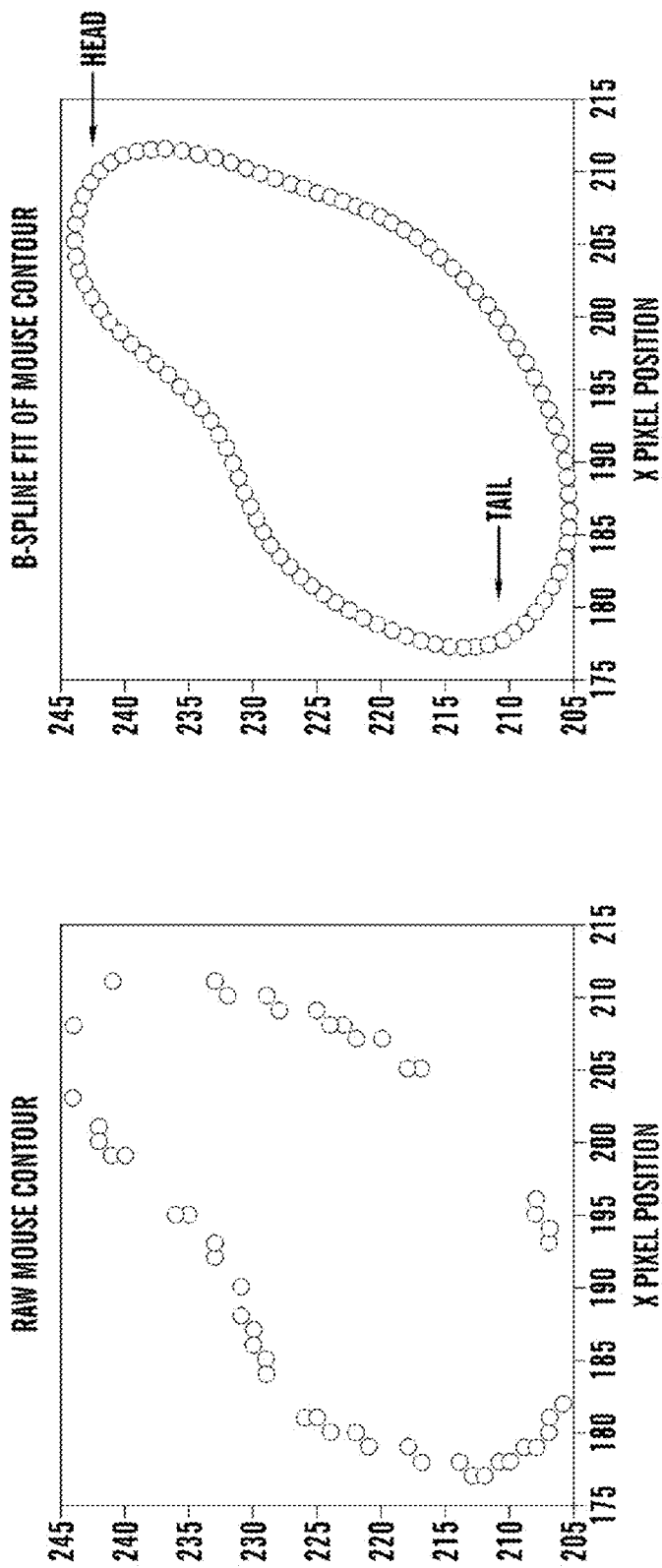
FIGS. 13A-13D depict discriminating head from tail using a depth camera.
Figure 13D:
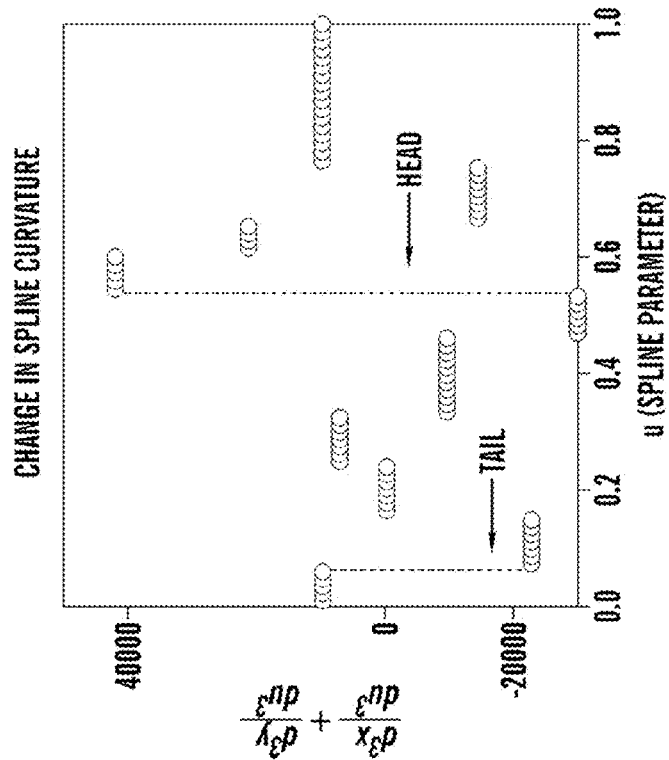
Figure 13C:
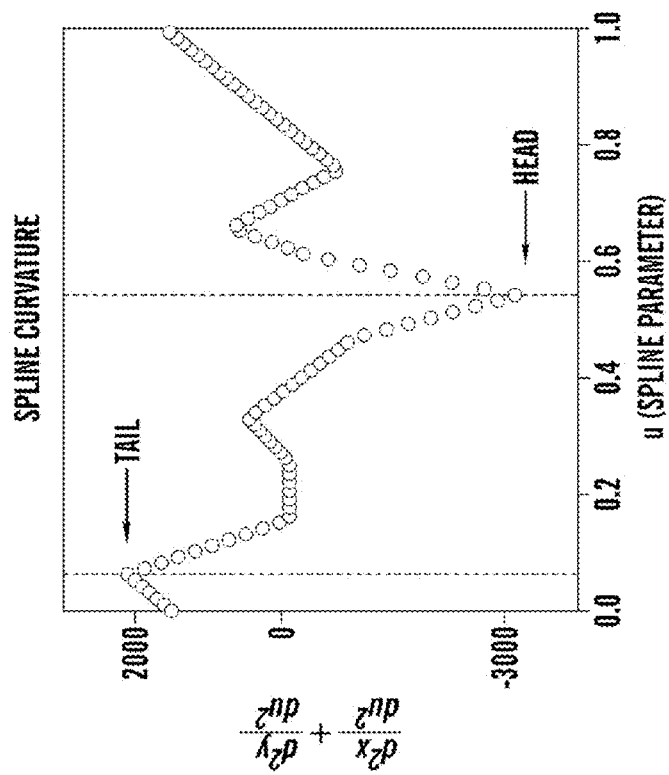

FIGS. 13A-13D generally relate to discriminating head from tail using a depth camera. (FIG. 13A) Raw contour data extracted from a depth camera image of a mouse. (FIG. 13B) Smoothing of the raw mouse contour using B-splines; each point in the spline fit (numbered 0 . . . u) is color coded red to blue for identification in (FIG. 13C-D). (FIG. 13C) Plotting curvature measurements reveals extrema that identify the head and tail (as marked with reference to the source image), but does not identify which is which (without supervision). (FIG. 13D) Taking an additional derivative identifies the less curved tail and the more curved head without supervision. Note that this method for identifying the head and tail of individual animals without surrogate markers or supervision is previously unreported and essential for assessing social interactions with a depth camera using QBPs.

Figure 14:
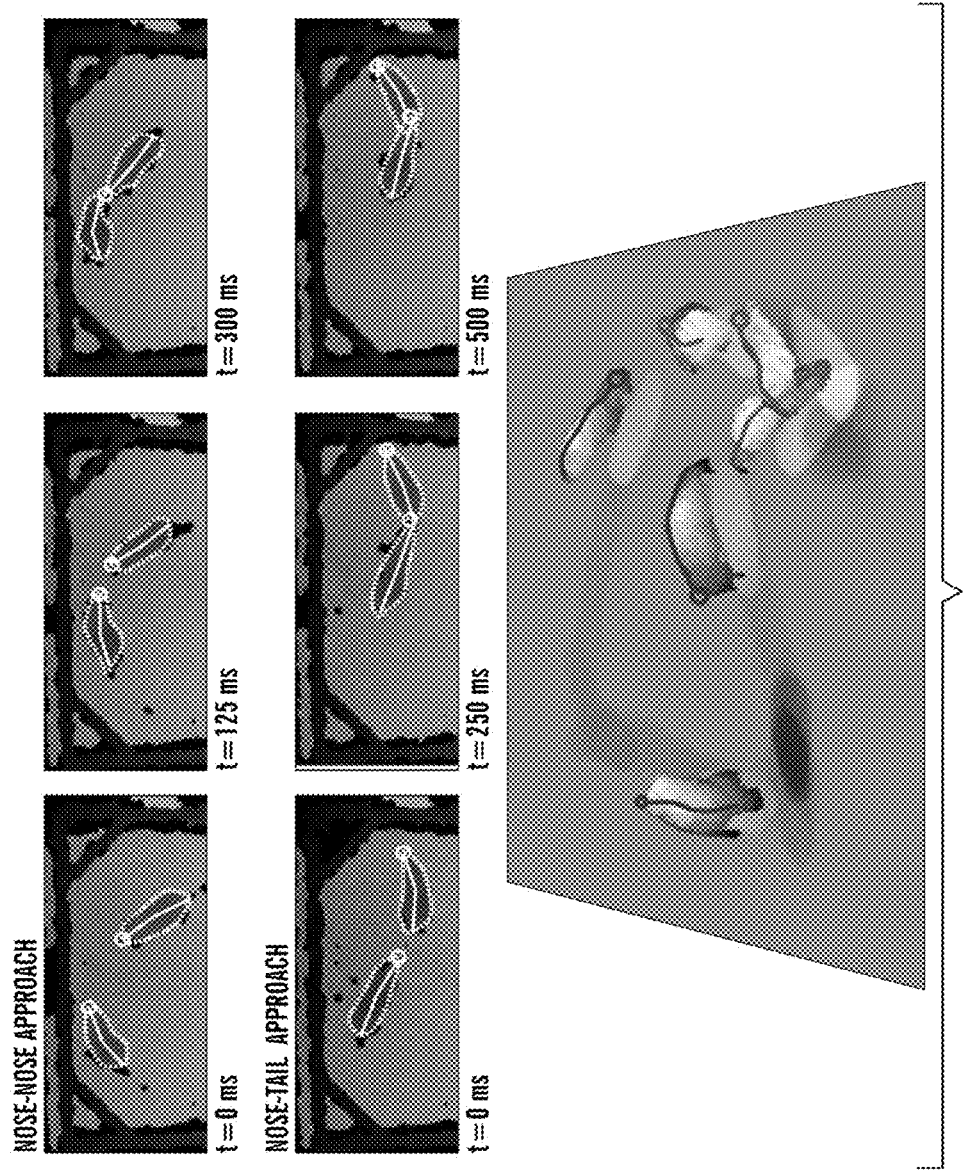
FIG. 14 depicts assessing social behaviors using depth cameras.

FIG. 14 generally relates to assessing social behaviors using depth cameras. (FIG. 14, Top) Using the algorithms described in FIGS. 13A-13D the present inventors can easily segment, identify and track two separate mice in the same experiment while following their head and tail; this additional reference data allows measurements of head-head and head-tail interaction. (FIG. 14, Bottom) Volume rendering of simultaneous tracking of two animals over time; three matched time points are shown as volumes, and average position is represented as color on the ground. Note this representation captures a tail-tail interaction between the two mice.

Figure 4C:
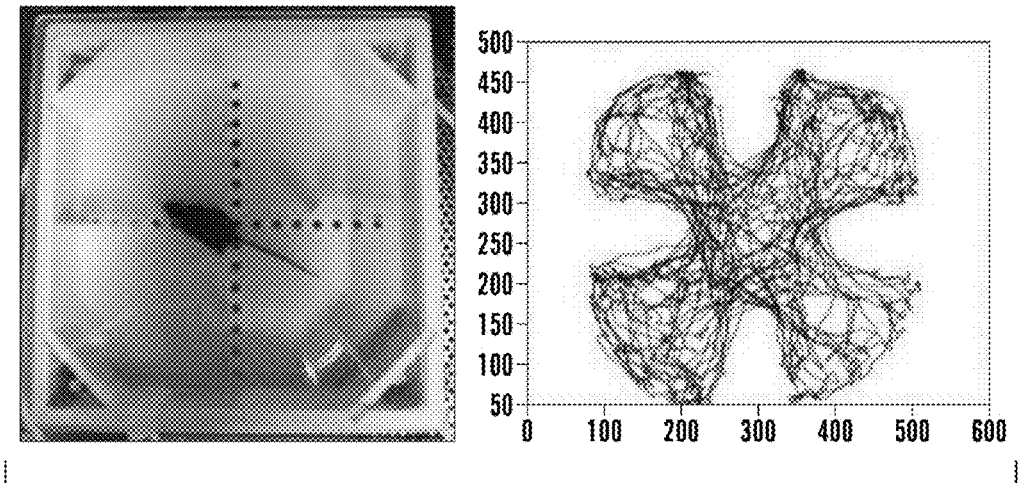
Figure 4D:
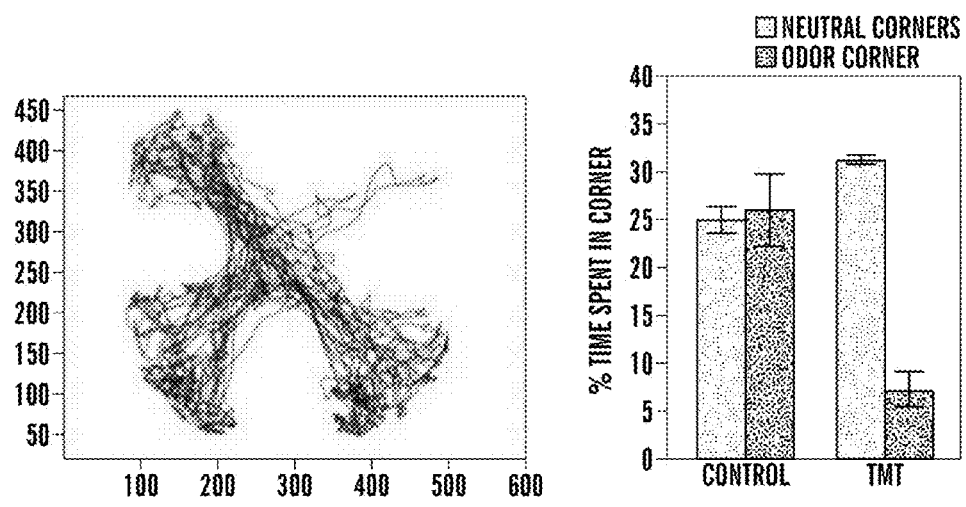
Figure 4E:
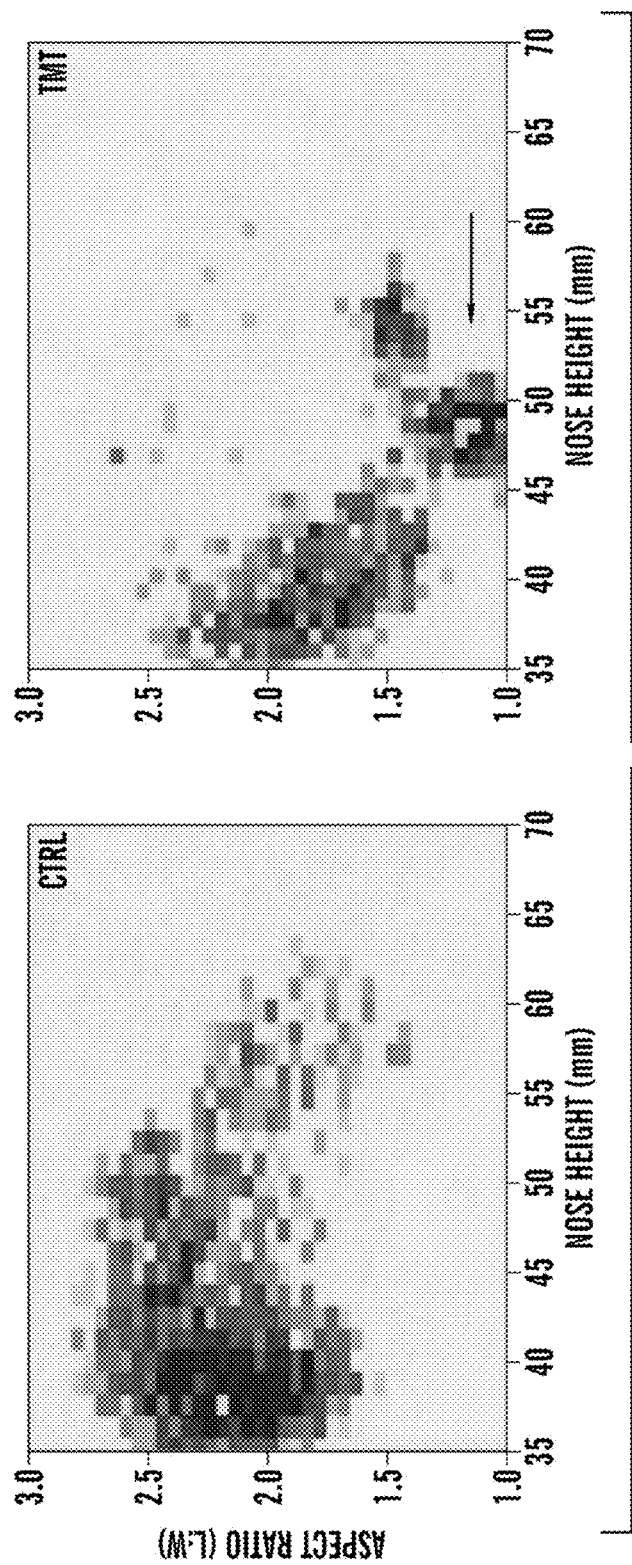

Consistent with the exquisite stimulus control afforded by the apparatus, the present inventors observe dramatic improvements in the behavioral avoidance exhibited by mice in response to predator cues delivered to one quadrant (FIG. 4C-4D). This approach, therefore, is extremely well-suited for testing the innate behavioral responses of ASD model mice to odorants, which collectively comprise the most important sensory stimulus driving behaviors in rodents. Importantly the present inventors can utilize the present inventors' depth camera approaches in this apparatus as well, enabling us to capture subtle behavioral responses to odorants that extend beyond changes in spatial location.

Technical Development for Acquisition and Analysis
Choice of Depth Camera

In the present invention, data can be acquired using an off-the-shelf Microsoft Kinect range camera without modification. This camera has the advantage of being inexpensive (<$150), widely-available and standardized, but the obligately large working distance and relatively low frame rate (24 fps) limits detection of fine detail, such as paw position. For example, the working distance of Kinect is, in practice, just under a meter. This limits the number of pixels sensed in the animal's body. With the Kinect, a 30 pixel by 45 pixel image of a mouse can be obtained. Cameras with sufficient resolution and working distance can be used to increase this size by about a factor of ten.

The present invention can utilize currently available depth cameras whose working distances are considerably smaller, whose frame rates are higher, i.e., up to 60 fps, preferably up to 100 fps and even more preferably up to 300 fps, and whose architecture is compatible both with the present inventors' behavioral apparatuses and data analysis workflow, including those from PMDTec, Fotonic and PrimeSense. By comparing these alternative range cameras in both home cage and odor-driven behavioral assays (described below), the best hardware platform for data acquisition is established.

For example, Kinect has an image acquisition rate of about 30 fps. 60 fps is desired. By maximizing the usable framerate, relatively faster body motions can be detected. Some of the mouse's natural actions are too fast for detection using 30 fps, such as very fast itching actions. A reasonable target framerate might be, for example, about 300 fps.

Choice of Analytical Methods

The software suite the present inventors have written can efficiently segment mice and extract large numbers of morphometric parameters describing the disposition of the mouse within any given arena (FIGS. 5A-5H, Table 1). As a proof-of-principle (described above) the present inventors have performed dimensional reduction on this datastream using PCA, and cluster analysis using K-means clustering methods (FIGS. 8, 9A-9B, 10 and 11). While these analytical methods are clearly sufficient to categorize various behavioral states, the specific methods used affect the degree to which the clusters are "chunked" into complex behaviors or into behavioral sub-states. The present inventors therefore further explore the consequences of using different data reduction techniques (including locally linear embedding, convolution neural networks and deep belief networks), clustering approaches (including the vector substitution heuristic, affinity propagation, fuzzy clustering, superparamagnetic clustering and random forests), and goodness-of-fit metrics (including the Akaike information criterion, the Bayesian Information Criterion, or a combination of the two) on the present inventors' ability to post-hoc assign natural language descriptors to defined QBPs; the present inventors have rapidly identified a suite of mathematical methods that allow different degrees of resolution of different behavioral states. The present inventors broaden the palette of system dynamics models (including the use of affinity propagation clustering on sliding window behavioral data, inferring state types and probabilities using Hidden Markov Models, and indirectly observing state-transition probabilities via deep belief networks) to more fully characterize how alterations in genotype or stimulus might alter behaviors as they evolve over time.

Characterize Home Cage, Juvenile Play and Social Approach Behaviors in three separate models for ASDs.

For these experiments the present inventors have chosen two specific mouse models: the Shank3 null model [16], because it has well-defined repetitive behaviors (likely to be effectively characterized by the present inventors' QBP analytical methods), and the Neuroligin3 null animals [17][41], because of their reported olfactory defects. Each of these strains has reasonable construct validity, as they were built based upon mutations found in patients with ASDs. The present inventors carried out this process in collaboration with an expert in the molecular underpinnings of ASDs, who is currently performing conventional behavioral screening in multiple ASD model mice lines, including those with mutations in MeCP2 and UBE3a [42][43]. The present inventors collaborated to perform small-scale characterization of chosen mouse lines in the home cage, juvenile play and social approach assays using conventional imaging and scoring methods; this enables establishment of ground-truth datasets to contextualize results generated using the new tracking and scoring methods of the present invention. In addition, the laboratory of the present inventors is a member of the Children's Hospital Boston IDDRC, a set of core facilities focused on developmental cognitive disorders. The IDDRC contains within it a comprehensive behavioral core facility that includes within in nearly every standard assay previously used to test the face validity of ASD model mice; when interesting or unexpected phenotypes using QBP analysis in the present assays are found, the mouse lines can be ported to the IDDRC for extensive conventional testing in areas of interest. All experiments described below are carried out using both males and females, at both 21 days of age and at 60 days of age, and experiments are set up using age, sex, and littermate-matched controls. Given the known behavioral effects of the Shank 3 ASD model mice and typical statistics for behavioral testing in ASD models [16][23], the present inventors tested at least about 15 pairs of animals per strain per age per gender in each of these behavioral assays. The product of this Aim is a rich set of conventional behavioral metrics and raw morphometric parameters (Table 1), describing the 3D behavior of these mice during home cage, social interaction and juvenile play behaviors, as well as the present inventors' QBP analysis of this dataset.

Assessing Home Cage Behavior in ASD Model Mice

The present inventors continuously monitor, for 60 hours intervals (through at least two circadian cycles) the home cage behavior of wild-type and mutant mice (as described above). The range cameras and analytical software according to the present invention can easily segment bedding, and the like, from the image of the mouse itself (FIGS. 5A-5H and 7); the present inventors implement a home cage monitoring system where the animals are held in standard 10.5"×19"×8" cages with gelled food and water within the cage itself, and a clear cage top, with a depth camera placed above the cage top. The present inventors capture conventional unsupervised behavioral metrics that enable calculation of diurnal activity patterns, distance traveled, and the like, as well as complex morphometric parameters to calculate QBPs. The present inventors also characterize the static and dynamic differences in QBP patterns between genotypes using the methods above. Post-hoc the present inventors also attempt to identify the behaviors exhibited during any given QBPs via video and data review, focusing in particular on identifying those behaviors that were captured by the HomeCageScan system during the prior home cage characterization of the 16p11.2 mice (including twitching, grooming, stretching, jumping, rearing, sniffing and walking) [20]. The present inventors test 15 animals×4 genotypes×2 genders×2 ages=240 total animals in this behavioral paradigm.

Assessing Social Interaction Behaviors in ASD Model Mice

The present inventors monitor social interaction behaviors using a standard three-chamber interaction apparatus modified for data acquisition using depth cameras [8][9][44]. The present inventors test animals in this modified apparatus using well-established protocols (10 minutes habituation and a 10 minute trial distinguishing between a novel inanimate object in one chamber and a pre-habituated novel conspecific animal held in a "cage" in the other chamber); data suggests that depth cameras can be effectively used to track mice within this apparatus during a typical experiment (FIG. 7). The present inventors perform data analysis as described above for Subaim A, with an emphasis on automated detection of sniff events within the novel chamber. The present inventors test 15 animals×4 genotypes×2 genders 2 ages=240 total animals in this behavioral paradigm.

Assessing Juvenile Play in ASD Model Mice

The present inventors monitor juvenile play behavior using standard protocols in a 12×12 plexiglass arena with a range camera mounted from above [8][45]. Current tracking algorithms according to the present invention enable clear disambiguation of two animals during a natural interaction, and can clearly orient head from tail, enabling software according to the present invention to automatically identify nose-nose and nose-tail interactions between animals (FIGS. 13A-13D and 14). These interactive parameters are added to the set of morphometric parameters when cluster analysis is performed. Play behaviors are assessed only in 21-day-old juveniles in 30 minute bouts, with one of the two animals being a gender-matched wild-type non-littermate unfamiliar control. Data analysis is carried out as described for Subaim A, with an emphasis on identifying QBPs posthoc that capture inter-animal interactions (such as nose-nose touches, nose-tail touches, interanimal grooming, and the like). The present inventors test 15 animals×4 genotypes×2 genders×1 age=120 total animals in this behavioral paradigm.

Testing Innate Olfactory Behavioral Responses in ASD Model Mice

The present inventors have a novel and well-validated arena that can be used to effectively assesses innate attraction or aversion to purified monomolecular odorants (FIG. 4C, 4D, FIG. 12, see above). The present inventors test the behavioral responses of ASD model mice to a set of 10 behaviorally-relevant odors, including attractive food-derived odors, aversive predator odors, and female and male urine odors (Table 2).

TABLE 2

LIST OF INNATELY-RELEVANT ODORANTS TO ASSESS IN ASD-MODEL MICE

| | |
|---|---|
| 1. | Female Urine |
| 2. | Male Urine |
| 3. | Castrated Male Urine |
| 4. | TMT (Aversive, Fox Odor) |
| 5. | 2-PT (Aversive, Weasel Odor) |
| 6. | Butryric Acid (Aversive, Spoiled Food) |
| 7. | E-E-Farnesene (Attractive, Conspecific Urine) |
| 8. | MTMT (Attractive, Conspecific Urine) Eugenol (Attractive, Environmenal Odor) Dipropyl Glycerol (Neutral) |

These experiments are straightforward, and the present inventors can easily extract both spatial metrics (such as avoidance index) and QBPs in the arena in a typical 5-minute trial. The main challenge to these experiments is the number of animals required: 10 per odor per condition (i.e., age, genotype, gender), as each animal can only be tested once due to the lingering neuroendocrinological effects of encountering innately-relevant odor cues [46]. To make this experiment practical (given this constraint), the present inventors limit this experiment to adult animals, although the present inventors will test both genders. The present inventors test 10 odors×15 animals×4 genotypes×2 genders×1 age=1200 total animals in this behavioral paradigm. Despite this challenge, results obtained from this aim represent the first comprehensive effort to assess innate olfactory function in ASD mice.

Each of the above identified modules or programs corresponds to a set of instructions for performing a function described above. These modules and programs (i.e., sets of instructions) need not be implemented as separate software programs, procedures or modules, and thus various subsets of these modules may be combined or otherwise re-arranged in various embodiments. In some embodiments, a memory may store a subset of the modules and data structures identified above. Furthermore, the memory may store additional modules and data structures not described above.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described herein can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer-readable medium; or a combination thereof Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used herein differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be appreciated that the methodologies disclosed in this specification are capable of being stored on an article of manufacture to facilitate transporting and transferring such methodologies to computing devices. The term article of manufacture, as used herein, is intended to encompass a computer program accessible from any computer-readable device or storage media.

Although some of various drawings illustrate a number of logical stages in a particular order, stages which are not order dependent can be reordered and other stages can be combined or broken out. Alternative orderings and groupings, whether described above or not, can be appropriate or obvious to those of ordinary skill in the art of computer science. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to be limiting to the precise forms disclosed. Many modifications and variations are possible in view of the above teachings. The embodiments were chosen and described in order to best explain the principles of the aspects and its practical applications, to thereby enable others skilled in the art to best utilize the aspects and various embodiments with various modifications as are suited to the particular use contemplated.

REFERENCES

[1] Walsh, C. A., Morrow, E. M. & Rubenstein, J. L. R. Autism and Brain Development. *Cell* 135, 396-400, doi:10.1016/j.cell.2008.10.015 (2008).
[2] Geschwind, D. H. Autism: Many Genes, Common Pathways? *Cell* 135, 391-395, doi:10.1016/j.cell.2008.10.016 (2008).
[3] Geschwind, D. H. Advances in autism. *Annual review of medicine* 60, 367-380, doi:10.1146/annurev.med.60.053107.121225 (2009).
[4] Nestler, E. J. & Hyman, S. E. Animal models of neuropsychiatric disorders. *Nature Neuroscience* 13, 1161-1169, doi:10.1038/nn.2647 (2010).
[5] Moy, S. S. & Nadler, J. J. Advances in behavioral genetics: mouse models of autism. *Molecular Psychiatry* 13, 4-26, doi:10.1038/sj.mp.4002082 (2007).
[6] Bill, B. R. & Geschwind, D. H. Genetic advances in autism: heterogeneity and convergence on shared pathways. *Current Opinion in Genetics & Development* 19, 271-278, doi:10.1016/j.gde.2009.04.004 (2009).
[7] Abrahams, B. S. & Geschwind, D. H. Connecting genes to brain in the autism spectrum disorders. *Archives of neurology* 67, 395-399, doi:10.1001/archneurol.2010.47 (2010).
[8] Crawley, J. N. Mouse Behavioral Assays Relevant to the Symptoms of Autism. *Brain Pathology* 17, 448-459, doi:10.1111/j.1750-3639.2007.00096.x (2007).
[9] Silverman, J. L., Yang, M., Lord, C. & Crawley, J. N. Behavioural phenotyping assays for mouse models of autism. *Nature Reviews Neuroscience* 11, 490-502, doi:10.1038/nrn2851 (2010).
[10] Ferrero, D. M. & Liberles, S. D. The secret codes of mammalian scents. *Wiley Interdiscip Rev Syst Biol Med* 2, 23-33, doi:10.1002/wsbm.39 (2010).
[11] Stowers, L. & Logan, D. W. Olfactory mechanisms of stereotyped behavior: on the scent of specialized circuits. *Curr Opin Neurobiol*, doi:S0959-4388(10)00035-8 [pii] 10.1016/j.conb.2010.02.013 (2010).
[12] Su, C. Y., Menuz, K. & Carlson, J. R. Olfactory perception: receptors, cells, and circuits. *Cell* 139, 45-59 (2009).
[13] Ryan, B. C., Young, N. B., Moy, S. S. & Crawley, J. N. Olfactory cues are sufficient to elicit social approach behaviors but not social transmission of food preference in C57BL/6J mice. *Behavioural brain research* 193, 235-242, doi:10.1016/j.bbr.2008.06.002 (2008).
[14] Brennan, P. A. & Zufall, F. Pheromonal communication in vertebrates. *Nature* 444, 308-315, doi:10.1038/nature05404 (2006).
[15] Broad, K. D. & Keverne, E. B. in *Nature Neuroscience* Vol. 11 128-129 (2008).
[16] Peca, J. et al. Shank3 mutant mice display autistic-like behaviours and striatal dysfunction. *Nature* 472, 437-442, doi:10.1038/nature09965 (2011).
[17] Radyushkin, K. et al. Neuroligin-3-deficient mice: model of a monogenic heritable form of autism with an olfactory deficit. *Genes, Brain and Behavior* 8, 416-425, doi:10.1111/j.1601-183X.2009.00487.x (2009).
[18] Fairless, A. H., Shah, R. Y., Guthrie, A. J., Li, H. & Brodkin, E. S. Deconstructing Sociability, An Autism-Relevant Phenotype, in Mouse Models. *The Anatomical Record: Advances in Integrative Anatomy and Evolutionary Biology* 294, 1713-1725, doi:10.1002/ar.21318 (2011).
[19] Steele, A. D., Jackson, W. S., King, O. D. & Lindquist, S. The power of automated high-resolution behavior analysis revealed by its application to mouse models of Huntington's and prion diseases. *Proceedings of the National Academy of Sciences of the United States of America* 104, 1983-1988, doi:10.1073/pnas.0610779104 (2007).
[20] Horev, G. et al. Dosage-dependent phenotypes in models of 16p11.2 lesions found in autism. *Proceedings of the National Academy of Sciences* 108, 17076-17081, doi:10.1073/pnas.1114042108 (2011).
[21] Witt, R. M., Galligan, M. M., Despinoy, J. R. & Segal, R. Olfactory behavioral testing in the adult mouse. *Journal of visualized experiments: JOVE*, doi:10.3791/949 (2009).
[22] Kobayakawa, K. et al Innate versus learned odour processing in the mouse olfactory bulb. *Nature* 450, 503-508 (2007).
[23] Crawley, J. N. Behavioral phenotyping strategies for mutant mice. *Neuron* 57, 809-818, doi:10.1016/j.neuron.2008.03.001 (2008).
[24] Ou-Yang, T.-H., Tsai, M.-L., Yen, C.-T. & Lin, T.-T. An infrared range camera-based approach for three-dimensional locomotion tracking and pose reconstruction in a rodent. *Journal of neuroscience methods* 201, 116-123, doi:10.1016/j.jneumeth.2011.07.019 (2011).

[25] Tort, A. B. L. et al. A simple webcam-based approach for the measurement of rodent locomotion and other behavioural parameters. *Journal of neuroscience methods* 157, 91-97, doi:10.1016/j.jneumeth.2006.04.005 (2006).

[26] Spink, A. J., Tegelenbosch, R. A., Buma, M. O. & Noldus, L. P. The EthoVision video tracking system—a tool for behavioral phenotyping of transgenic mice. *Physiology & behavior* 73, 731-744 (2001).

[27] Verbeek, J. Rodent behavior annotation from video. (2005).

[28] Jhuang, H. et al. Automated home-cage behavioural phenotyping of mice. *Nature Communications* 1, 68, doi: 10.1038/ncomms1064 (2010).

[29] Benjamini, Y., Fonio, E., Galili, T., Havkin, G. Z. & Golani, I. Quantifying the buildup in extent and complexity of free exploration in mice. *Proceedings of the National Academy of Sciences* 108 Suppl 3, 15580-15587, doi: 10.1073/pnas.1014837108 (2011).

[30] Benjamini, Y. et al. Ten ways to improve the quality of descriptions of whole-animal movement. *Neuroscience and biobehavioral reviews* 34, 1351-1365, doi:10.1016/j.neubiorev.2010.04.004 (2010).

[31] Mayya, M. & Doignon, C. in 2011 *IEEE International Symposium on Robotic and Sensors Environments (ROSE)* 60-64 (IEEE, 2011).

[32] Tinbergen, N. *The study of instinct*. (Clarendon Press, 1951).

[33] Stella, M. & Kleisner, K. Uexkiillian Umwelt as science and as ideology: the light and the dark side of a concept. 129, 39-51, doi:10.1007/s12064-010-0081-0 (2010).

[34] Yildirim, E. & Birnbaumer, L. TRPC2: molecular biology and functional importance. *Handb Exp Pharmacol*, 53-75 (2007).

[35] Wang, Z. et al. Pheromone detection in male mice depends on signaling through the type 3 adenylyl cyclase in the main olfactory epithelium. *J Neurosci* 26, 7375-7379, doi:26/28/7375 [pii] 10.1523/JNEUROSCI.1967-06.2006 (2006).

[36] Wang, Z., Nudelman, A. & Storm, D. R. Are pheromones detected through the main olfactory epithelium? *Mol Neurobiol* 35, 317-323, doi:MN:35:3:317 [pii] (2007).

[37] Mandiyan, V. S., Coats, J. K. & Shah, N. M. Deficits in sexual and aggressive behaviors in Cnga2 mutant mice. *Nat Neurosci* 8, 1660-1662 (2005).

[38] Restrepo, D., Arellano, J., Oliva, A. M., Schaefer, M. L. & Lin, W. Emerging views on the distinct but related roles of the main and accessory olfactory systems in responsiveness to chemosensory signals in mice. *Horm Behav* 46, 247-256 (2004).

[39] Kimchi, T., Xu, J. & Dulac, C. A functional circuit underlying male sexual behaviour in the female mouse brain. *Nature* 448, 1009-1014, doi:10.1038/nature06089 (2007).

[40] Yang, M. & Crawley, J. N. Simple behavioral assessment of mouse olfaction. *Current protocols in neuroscience/ editorial board, Jacqueline N. Crawley . . . [et al]* Chapter 8, Unit 8.24, doi:10.1002/0471142301.ns0824s48 (2009).

[41] Südhof, T. C. Neuroligins and neurexins link synaptic function to cognitive disease. *Nature* 455, 903-911, doi: 10.1038/nature07456 (2008).

[42] Greer, P. L. et al. The Angelman Syndrome Protein Ube3A Regulates Synapse Development by Ubiquitinating Arc. *Cell* 140, 704-716, doi:10.1016/j.cell.2010.01.026 (2010).

[43] Cohen, S. & Greenberg, M. E. Communication Between the Synapse and the Nucleus in Neuronal Development, Plasticity, and Disease. *Annual Review of Cell and Developmental Biology* 24, 183-209, doi:10.1146/annurev.cellbio.24.110707.175235 (2008).

[44] Moy, S. S. et al. Social approach in genetically engineered mouse lines relevant to autism. *Genes, Brain and Behavior* 8, 129-142, doi:10.1111/j.1601-183X.2008.00452.x (2009).

[45] Pe-agarikano, O. et al. Absence of CNTNAP2 Leads to Epilepsy, Neuronal Migration Abnormalities, and Core Autism-Related Deficits. *Cell* 147, 235-246, doi:10.1016/j.cell.2011.08.040 (2011).

[46] Fendt, M., Endres, T., Lowry, C. A., Apfelbach, R. & McGregor, I. S. TMT-induced autonomic and behavioral changes and the neural basis of its processing. *Neurosci Biobehav Rev* 29, 1145-1156 (2005).

We claim:

1. A method for automatically discovering, characterizing and classifying the behavior of an animal in an experimental area, comprising:
    (a) using a 3D depth camera to obtain a video stream having a plurality of images of the experimental area with the animal in the experimental area, the images having both area and depth information;
    (b) removing background noise from each of the plurality of images to generate processed images having light and dark areas;
    (c) determining contours of the light areas in the plurality of processed images;
    (d) extracting parameters from both area and depth image information within the contours to form a plurality of multi-dimensional data points, each data point representing the posture of the animal at a specific time and identifying the animal's head and tail based on a derivative of the contour curvature;
    (e) clustering the data points at each specific time to output a set of clusters that are segmented form each other so that each cluster represents an animal behavior;
    (f) assigning each cluster a label that represents an animal behavior; and
    (g) outputting a visual representation of the set of clusters and corresponding labels.

2. The method of claim 1 wherein step (b) comprises:
    (b1) using the 3D depth camera to obtain a video stream having a plurality of baseline images of the experimental area without an animal present;
    (b2) generating a median of the baseline images to form a baseline depth image;
    (b3) subtracting the baseline depth image from each of the plurality of images obtained in step (a) to produce a plurality of difference images;
    (b4) performing a median filtering operation on each difference image to generate a filtered difference image; and
    (b5) removing image data that is less than a predetermined threshold from each of the plurality of filtered difference images to generate the processed images.

3. The method of claim 1, wherein step (c) comprises determining contours of all light regions in each processed image with a contour detection algorithm and tracking each contour with a Kalman filter.

4. The method of claim 1, wherein the label for each cluster is requested by a user interface after displaying video data representing each cluster.

5. The method of claim 1, wherein the behavior comprises a quantitative behavior primitive.

6. An apparatus for automatically discovering, characterizing and classifying the behavior of an animal in an experimental area, comprising:

a 3D depth camera that generates a video stream having a plurality of images of the experimental area with the animal in the experimental area, the images having both area and depth information;

a data processing system having a processor and a memory containing program code which, when executed:

(a) removes background noise from each of the plurality of images to generate processed images having light and dark areas;

(b) determines contours of the light areas in the plurality of processed images;

(c) extracts parameters from both area and depth image information within the contours to form a plurality of multi-dimensional data points, each data point representing the posture of the animal at a specific time and identifies the animal's head and tail based on a derivative of the contour curvature; and (d) clusters the data points to output a set of clusters that each represent an animal behavior;

(e) assigns each cluster a label that represents an animal behavior; and (f) outputs a visual representation of the set of clusters and corresponding labels.

7. The apparatus of claim 6, wherein the 3D depth camera obtains a video stream having a plurality of baseline images of the experimental area without an animal present and wherein step (a) comprises:

(a1) generating a median of the baseline images to form a baseline depth image;

(a2) subtracting the baseline depth image from each of the plurality of images obtained in step (a) to produce a plurality of difference images;

(a3) performing a median filtering operation on each difference image to generate a filtered difference image; and (a4) removing image data that is less than a predetermined threshold from each of the plurality of filtered difference images to generate the processed images.

8. The apparatus of claim 6, wherein the label for each cluster is requested after displaying video data representing each cluster.

9. The apparatus of claim 6, wherein the behavior comprises a quantitative behavior primitive.

10. The apparatus of claim 6, wherein step (b) comprises determining contours of all light regions in each processed image with a contour detection algorithm and tracking each contour with a Kalman filter.

11. The apparatus of claim 6 wherein in step (c) parameters extracted from area information with each contour include at least one of perimeter, surface area rotation angle and length.

12. The apparatus of claim 6, wherein in step (c) parameters extracted from depth information with each contour include at least one of height, width, depth, velocity spine curvature and limb position.

13. The apparatus of claim 6, wherein step (d) comprises reducing covariance between data points and clustering the reduced covariance data points with a clustering method.

14. The apparatus of claim 6, wherein covariance between data points is reduced by reducing dimensionality of each data point.

15. The apparatus of claim 14, wherein the dimensionality of each data point is reduced by applying at least one of principal components analysis, singular value decomposition, independent components analysis and locally linear embedding to the points.

* * * * *